United States Patent
Daneshmand et al.

(10) Patent No.: US 10,175,179 B2
(45) Date of Patent: Jan. 8, 2019

(54) APPARATUS AND METHOD FOR HIGH RESOLUTION COMPLEX PERMITTIVITY SENSING USING HIGH Q MICROWAVE SENSORS FOR LOSSY OR NON-LOSSY MEDIUMS AND SAMPLES

(71) Applicant: The Governors Of The University Of Alberta, Edmonton (CA)

(72) Inventors: Mojgan Daneshmand, Edmonton (CA); Mohammad Hossein Zarifi, Edmonton (CA)

(73) Assignee: The Governors Of The University Of Alberta, Edmonton (CA)

(*) Notice: Subject to any disclaimer, the term of this patent is extended or adjusted under 35 U.S.C. 154(b) by 285 days.

(21) Appl. No.: 14/869,805

(22) Filed: Sep. 29, 2015

(65) Prior Publication Data

US 2016/0091544 A1  Mar. 31, 2016

Related U.S. Application Data

(60) Provisional application No. 62/111,570, filed on Feb. 3, 2015, provisional application No. 62/057,010, filed on Sep. 29, 2014.

(51) Int. Cl.
*G01N 24/08* (2006.01)
*G01N 22/00* (2006.01)

(52) U.S. Cl.
CPC .................. *G01N 22/00* (2013.01)

(58) Field of Classification Search
CPC .................................................. G01N 22/00
(Continued)

(56) References Cited

U.S. PATENT DOCUMENTS 5,652,556 A  7/1997 Flory et al.
6,496,147 B1 12/2002 Kirino
(Continued)

FOREIGN PATENT DOCUMENTS

WO  2004107498 A2  12/2004
WO  2014190062 A1  11/2014

OTHER PUBLICATIONS

M. Zheng et al., "Cavity control of active integrated antenna oscillators", IEEE Proc.-Microw. Antennas Propag., vol. 148, No. 1, Feb. 2001.
A. Mark Jones et al., "Design considerations for high-Q bandpass microwave oscillator sensors based upon resonant amplification", Applied Physics Letters 104, 253507, Jun. 26, 2014.
(Continued)

*Primary Examiner* — Farhana Hoque
(74) *Attorney, Agent, or Firm* — Moffat & Co

(57) ABSTRACT

Apparatuses and methods for non-contact sensing of physical or chemical properties of a target sample using a planar microwave resonator are provided. In one aspect, a planar microwave resonator is used in combination with an active feedback loop for increasing the quality factor of the resonator to compensate for an existing signal loss in the sample or environment. In another aspect, an active feedback loop is used in combination with a microwave resonator to compensate for signal loss in a lossy medium. In another aspect, a planar microwave resonator comprising a secondary layer defining a sensing interface may be used to facilitate the sensing by exposing the secondary layer to a substance to be investigated. In another aspect, a planar microwave resonator sensor is provided comprising separate resonator and active feedback loop components that are indirectly connected through an electromagnetically coupling and may be constructed on two separate support structure.

14 Claims, 14 Drawing Sheets

(58) Field of Classification Search
USPC .................................. 324/633, 316, 636
See application file for complete search history.

(56) References Cited

U.S. PATENT DOCUMENTS

| | | | |
|---|---|---|---|
| 8,823,391 | B2 | 9/2014 | Jones et al. |
| 2005/0026571 | A1 | 2/2005 | Yang et al. |
| 2005/0099222 | A1 | 5/2005 | Yang |
| 2005/0270122 | A1 | 12/2005 | Hyman et al. |
| 2007/0091008 | A1 | 4/2007 | Mortazawi |
| 2007/0139117 | A1 | 6/2007 | Iida |
| 2007/0285314 | A1 | 12/2007 | Mortazawi et al. |
| 2011/0057653 | A1* | 3/2011 | Barmatz ............ G01R 33/1223 324/316 |
| 2012/0050107 | A1 | 3/2012 | Mortazawi et al. |
| 2013/0207670 | A1* | 8/2013 | Jones .................. H03B 5/1817 324/636 |

OTHER PUBLICATIONS

Morteza, Nick, "Low Phase-Noise Planar Oscillators Based on Low-Noise Active Resonators". IEEE Transactions on Microwave Theory and Techniques, vol. 58, No. 5, May 2010.

Kai Chang et al., "Active Integrated Antennas", IEEE Transactions on Microwave Theory and Techniques, vol. 50, No. 3, Mar. 2002.

P. Bowron et al., "A Classification of Multiple-Source Feedback Filters". Circuit Theory and Applications, vol. 11, 279-287, 1983.

M. Penza et al., "Relative humidity sensing by PVA-coated dual resonator SAW oscillator", Sensors and Actuators B 68, 300-306, 2000.

A. Mark Jones et al., "Regenerative feedback resonant circuit to detect transient changes in electromagnetic properties of semi-insulating materials", Review of Scientific Instruments 84, 084703, Aug. 8, 2013.

Naser Qureshi et al., "An active resonator based on magnetic films for near field microwave microscopy", Journal of Applied Physics 111, 07A504, Feb. 17, 2012.

* cited by examiner

L2 = 5cm

L2 = 8cm

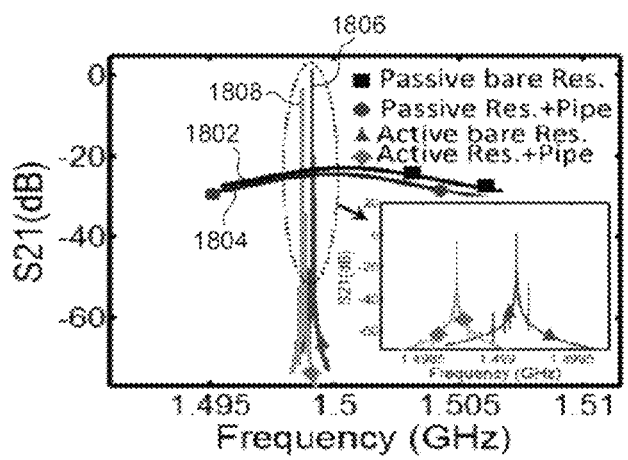
FIG. 18
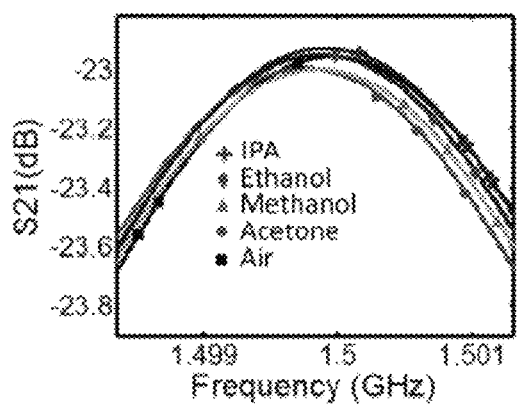 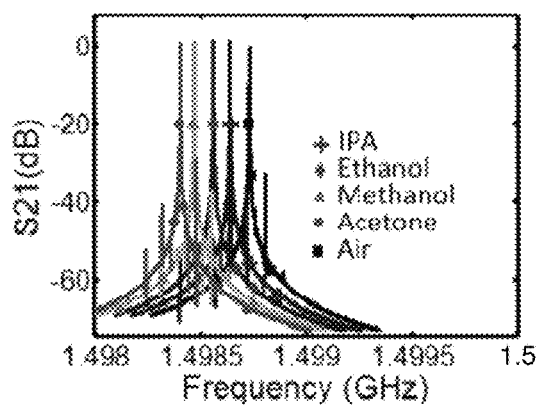
FIG. 19A        FIG. 19B

APPARATUS AND METHOD FOR HIGH RESOLUTION COMPLEX PERMITTIVITY SENSING USING HIGH Q MICROWAVE SENSORS FOR LOSSY OR NON-LOSSY MEDIUMS AND SAMPLES

CROSS-REFERENCE TO RELATED APPLICATIONS

This application claims the benefit of U.S. Provisional Application 62/057,010 filed Sep. 29, 2014 and U.S. Provisional Application 62/111,570 filed Feb. 3, 2015, both of which are incorporated herein by reference in their entireties.

FIELD OF THE DISCLOSURE

The present disclosure relates generally to sensors for sensing chemical and physical properties of a sample or an environment, and more particularly to sensors comprising a planar microwave resonator.

BACKGROUND

Microwave resonators are used in various sensing applications ranging from material identification and classification, gas sensing and detection, and environmental system monitoring, to name but a few. One type of resonator is a microwave planar split-ring resonator, which has a planar structure with a simple, low-cost fabrication process and operation form factor. A planar resonator allows for non-contact sensing, and easy integration and compatibility with complementary metal oxide semiconductor (CMOS) technologies. Resonators have been used in microfluidic devices for the label-free detection of biomolecules and the detection of various concentrations of a target material in solution.

A planar split-ring resonator detects the variation in a nearby medium through variations in the electric field above a substrate of the resonator. However, planar resonators generally suffer from low sensitivity and resolution since they have a low quality factor (Q factor), for example up to 300. The quality factor is a dimensionless parameter that represents energy losses in an under damped oscillator or resonator. A definition of quality factor (Q) is the ratio of the energy stored in the oscillating resonator to the energy dissipated per cycle by damping. Quality factor of a resonator also is defined by the resonance frequency divided by bandwidth of the signal. This also means for higher quality factors, the signal has smaller bandwidth.

As a result of planar resonators having a low quality factor, the distance between a sample being investigated and the resonator is typically minimized to attempt to optimize the effects of the sample on the electric field. In this regard, the resonators have a small field of view. Also, the low quality factor does not allow for small variation detection. Bringing the sample as close as possible would make the effect of the sample variation more detectable. Furthermore, the permittivity sensing resolution of passive planar resonator sensors having a low quality factor is also low, particularly when the sample or the environment through which the sample is sensed is lossy (e.g. absorbs part of the signal emitted by the sensor). A lossy sample or environment degrades the quality factor of the sensor, which in turn reduces the accuracy and resolution of the sensor.

SUMMARY

In one aspect, the present disclosure is directed to a method for high resolution microwave sensing of a sample in the presence of a lossy medium, the method comprising: increasing the quality factor of a passive planar microwave resonator to a first value with an active regenerative feedback loop; positioning the lossy medium and the planar microwave resonator in proximity to one another, thereby decreasing the quality factor of the planar microwave resonator to a second value; adjusting the active feedback loop to compensate for signal energy loss of the planar microwave resonator due to the lossy medium, where the adjusting raises the quality factor to a third value that is higher than the second value; positioning the sample and the planar microwave resonator in proximity to one another such that the resonator signal passes through the lossy medium to sense the sample variation; and measuring at least one of resonance frequency, quality factor, and amplitude of a signal of the planar microwave resonator in response to the excitation of the resonator in proximity to the sample.

In another aspect, the present disclosure is directed to a method for microwave sensing of a sample or a physical stimulation, the method comprising: positioning a secondary layer proximate to a planar microwave resonator comprising an active regenerative feedback loop; exposing the secondary layer to the sample or physical stimulation; applying a signal to the planar microwave resonator to excite the resonator; and measuring, after the exposing, a value or the variation of at least one of resonance frequency, quality factor, and amplitude of a signal of the planar microwave resonator in response to the excitation of the resonator in proximity to the secondary layer.

In another aspect, the present disclosure is directed to a method for microwave sensing of a sample, the method comprising: positioning a passive planar microwave resonator in proximity to the sample, the planar microwave resonator disposed at a first support structure, wherein the planar microwave resonator is electromagnetically, electrically or magnetically coupled to at least one feed line and to an active feedback loop, the active feedback loop disposed at a second support structure separate from the first support structure; applying a microwave signal at the feed line to excite the planar microwave resonator through the coupling between the feed line and the resonator, where a quality factor of the passive resonator is increased by the active feedback loop; and measuring at least one of resonance frequency, quality factor, and amplitude of a signal of the planar microwave resonator at the first or second feed line in response to the excitation of the resonator in proximity to the sample.

BRIEF DESCRIPTION OF THE DRAWINGS

The present disclosure will be better understood having regard to the drawings in which:

FIG. 17A is a graph showing S21 parameter simulation results for the resonator sensor of FIG. 15 with the tube both present and not present, and the active feedback loop turned on;

FIG. 18 is a graph showing measurements of the S21 parameter for both the active and passive resonator, and both with and without tube positioned proximate the resonator;

FIG. 19A is a graph showing S21 measurements of the resonator in passive mode when various liquids were passed through the tube;

FIG. 19B is a graph showing S21 measurements of the resonator in passive mode when various liquids were passed through the tube;

DETAILED DESCRIPTION

Figure 1:
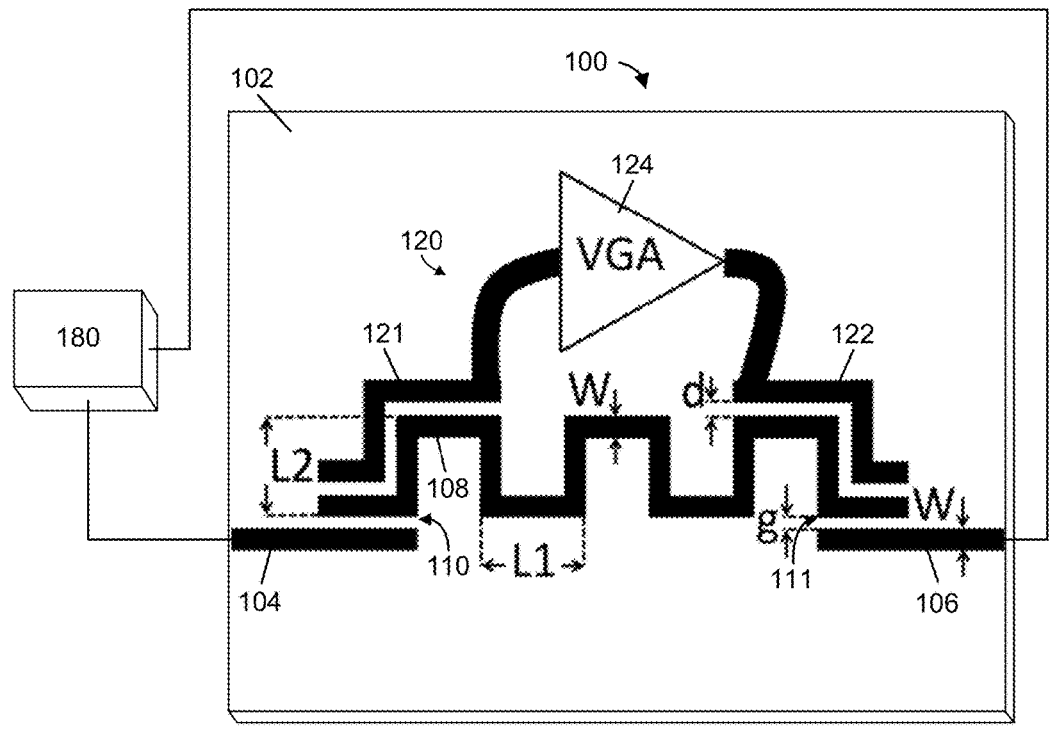
FIG. 1 is a schematic of an example planar microwave resonator according to the present disclosure.

This disclosure provides various embodiments for sensing chemical and physical properties of a sample or an environment using microwave resonators. In one aspect, a planar microwave resonator is used in combination with an active feedback loop for increasing the quality factor of the resonator to compensate for an existing loss in the environment. A higher quality factor may increase one or more of the sensitivity, resolution, field of view, and minimum detectable signal of the sensor. In another aspect, an active feedback loop is used in combination with a planar microwave resonator sensor to compensate or adapt for signal loss in or across a lossy medium. The gain of an amplifier in the active feedback loop may be adjusted to retrieve the resonator signal and increase the quality factor above its reduced level. The gain of the active feedback loop may be also adjusted to change the dynamic range of the sensor (dynamic range is defined by the range of the trackable complex permittivity variation and in practice it is referred to the types of the materials that can be monitored).

In another aspect, the present disclosure is directed to a planar microwave resonator with an active regenerative feedback loop comprising a secondary layer defining a sensing interface, which may be used to facilitate the sensing by exposing the secondary layer to a substance or a physical stimulation to be investigated. Properties of the substance or physical stimulation, herein referred to as a sample, may be investigated or determined based on the changes in the properties of the secondary layer sensed by the resonator sensor. The secondary layer may increase the surface area and adsorb more target molecules compared to a bare resonator, and thus may create a more discernable change in electrical properties of the secondary layer. In addition, the physical or chemical characteristics of a secondary layer may vary as a result of a change in the environment and the microwave resonator may read the change in the secondary layer. This may allow for more accurate or higher resolution sensing of the sample.

In another aspect, the present disclosure is directed to a planar microwave resonator with an active regenerative feedback loop, the sensor comprising separate passive resonator and active feedback loop components that are indirectly connected through an electromagnetically coupling as opposed to a direct metallic connection. Such a sensor may be used in applications where there may be a benefit to physically separating the passive resonator from the active feedback loop. For example, the passive resonator section may be embedded in a non-accessible environment. The passive resonator may have no direct power connection. The active section may be located in an accessible environment and may be connected to a power source.

Active Feedback Loop

Existing microwave resonator sensors that do not have an active feedback loop typically suffer from low sensitivity and low resolution since the resonator has a low quality factor (e.g. up to 300). Consequently, in previous sensor configurations, the distance between the sample and the resonator was minimized so as to optimize the effects of the electric field at the sample. In other words, the resonator was positioned as close as possible to the sample. Furthermore, lossy mediums, such as an aquatic medium, are normally harmful for microwave devices since a significant portion of the microwave energy is absorbed (e.g. lost) by the medium, thereby reducing the quality factor of the device. This reduces the minimum detectable permittivity of the resonator.

The term sample is generally used herein to refer to any gas, fluid, solid, chemical, biological matter, material or any other matter, or stimulation, or any combination thereof, that is to be investigated using a microwave resonator sensor.

In one aspect, the present disclosure is directed to a planar microwave resonator for measuring the complex permittivity of different materials comprising an active feedback loop employed to increase (e.g. boost) the quality factor of the resonator. The active feedback loop may also be referred to as a constructive feedback loop or a regenerative feedback loop. In some embodiments, the loop may be a positive feedback loop. Quality factor in a resonant sensor typically plays an important role since it determines the sensitivity, resolution and minimum detectable signal of the sensor. A microwave device with a high quality factor can lead to a sensing platform with higher sensitivity and resolution with respect to its conventional counterparts.

An amplified signal produced by the active feedback loop may compensate for the energy loss of the signal in a lossy environment and enable high resolution microwave sensing in a lossy medium. The amplified signal generally also increases the strength of the electric field of the resonator, which results in an increase in the depth of penetration of the electric field. In this sense, the field of view of the resonator (for lossy and non lossy environments) is enhanced, which may allow for improved noncontact sensing in different environments.

Improved sensing may include utilizing an enhanced field of view and achieving higher resolution permittivity sensing, meaning a sensor device has the capability of detecting very small variations in the permittivity of a sample in a lossy or non lossy medium. In addition, improved sensing may comprise utilizing an enhanced field of view of the resonator to allow the sample being investigated to be located farther away from the resonator rather than being in contact or very close to the resonator. This may be advantageous in some sensing applications where it may be more desirable to position the sensor at a spaced away location from the sample being investigated rather than having to position the sensor right at or very close to the sample. Depending on the sensing application, it may be difficult, expensive, or even impractical to position the sensor in contact with the sample to be investigated. One non-limiting example is the sensing of a gas or liquid in a pipe, tube or container. In some situations, it may be simpler to position a sensor at the exterior of the pipe or container rather than within the pipe or container.

The term lossy medium as used herein generally refers to a medium that is more lossy than air. An enhanced field of view may also allow for the sample being investigated being located farther away from the resonator rather than being in contact or very near to the resonator, even in a lossy medium. This may allow for non-invasive monitoring and sensing. Put another way, a lossy medium has a complex permittivity with higher imaginary part than air (or a vacuum, which has a permittivity with imaginary part of being zero). The imaginary part of the permittivity is also based on the fact that the response of a material to external fields generally depends on the frequency of the field (as oppose to a vacuum). This frequency dependence reflects the fact that the polarization of a material does not respond instantaneously to an applied field and therefore causes loss of the microwave signal. The active regenerative feedback loop may compensate for such microwave losses and enable high resolution sensing with larger field of view sensing in the presence of such a medium.

A planar microwave resonator comprising an active regenerative feedback loop may have physically separate active and passive components. These components may be positioned at different layers, formed as different physical pieces, etc. The passive component is the resonance part (e.g. resonator) and the active component is the active regenerative feedback loop. The active and passive components of the sensor may be electromagnetically, electrically or magnetically coupled to one another. The active feedback loop may be used to enhance the quality factor of the passive resonator that is coupled to the feedback loop. Furthermore, since the regenerative feedback loop is a separate physical component, the feedback loop may be positioned in a different physical area (e.g. an accessible area, etc.) than the passive resonator component. Also, the feedback loop may generally be connected to a power source, while the passive resonator is not. The can allow the passive resonator component to be integrated, encapsulated or implanted in a non-accessible medium or area (e.g. within a pipe, container, etc.).

The planar microwave resonator comprising separate active and passive components may be used in several applications, including but not limited to high-resolution implantable biosensors for monitoring biological or physiological sensing where the passive section is implanted in a human or animal body with no direct DC power requirement and the active circuit can be taped on the outside of the body or assembled on wearable clothing or accessories. Alternatively or additionally, the passive section may be used for chemical sensing in oil-gas applications when the passive resonator component is integrated inside a non metallic pipe or container and the active component is positioned outside of the pipe and may be powered by chemical batteries, solar batteries or other DC power feeding or harvesting techniques.

A planar microwave resonator comprising an active feedback loop employed to increase the quality factor of the resonator may be used various applications, including but not limited to material identification, material characterization, liquid concentration sensing, liquid mixture monitoring, liquid or material interface sensing, sample time or transient variation monitoring, sensing of a sample through a lossy medium, real-time monitoring of adsorbents performance in gas trapping, in pollutant monitoring, in environment monitoring, and in harsh or unreachable environments.

FIG. 1 is an example planar microwave resonator 100 in which embodiments of the present disclosure may be implemented. Resonator 100 is a meander-type resonator, however, other types of resonators may be used, such as ring-type, loop-type, line-type, and triangular-type resonators, or a combination thereof in the form of a single resonator or multi resonators.

Resonator 100 may comprise a substrate 102. Input and output signals of resonator 100 may be coupled to the resonator through two microstrip feed lines 104 and 106, respectively, and the capacitive coupling between them and the open resonator loop 108. Feed line 104 may be a first port of the device (e.g. port 1), and line 106 may be a second port (e.g. port 2). A signal may be inputted to a feed line to generate a resonant frequency of the resonator. Furthermore, an output signal may be obtained at a feed line to be transmitted elsewhere and possibly analyzed or processed by another device, such as a spectrum analyzer, a network analyzer, or other computing device. The device can be also characterized directly by network analyzers. The region located between resonator loop 108 and each of feed lines 104, 106 is referred to as a coupling gap 110 and 111, respectively. In addition, the distance between each feed line 104, 106 and the resonator loop 108 is indicated with letter 'g'.

Resonator 100 further comprises an active feedback loop 120 having feedback lines 121 and 122, and an active device 124 such as a variable gain amplifier. Feedback loop 120 is capacitively coupled the resonator to reduce the direct current (DC) loading effect on the resonator. In some embodiments, the amplifier may be a transistor, such as a bipolar-junction transistor (BJT). A BJT transistor may be a common emitter amplifier. In some embodiments, a low noise, high gain transistor from California Eastern Laboratories (CEL) may be used.

Resonator 100 may be used in combination with other equipment or components 180, such as a processor, microcontroller, a volatile memory, a non-volatile memory, a communications system, a microwave oscillator, a signal processing system, a data storage system, a computing device, analog circuitry, etc. However, this other equipment and other component(s) 180 are not shown in any detail for the sake of simplicity.

Electrical conductors, such as one or more of feed lines 104, 106, resonator loop 108, and feedback lines 121, 122 may comprise any suitable material, such as copper.

A coupling gap (e.g. 110, 111) and its associated capacitance is one of if not the most sensitive area at the planar microwave resonator to variations in the complex permittivity in the vicinity of the resonator. In other words, the coupling gaps of the resonator have the highest microwave field intensity. Therefore in some embodiments, one of coupling gaps 110, 111 of resonator 100 may be positioned in substantial alignment with the sample or material to be investigated using the sensor. In some embodiments having a different type of planar resonator, the sensitive location may be different. For example, a sensitive region may be a different coupling gap or another region or coupling area at the resonator.

Figure 2:
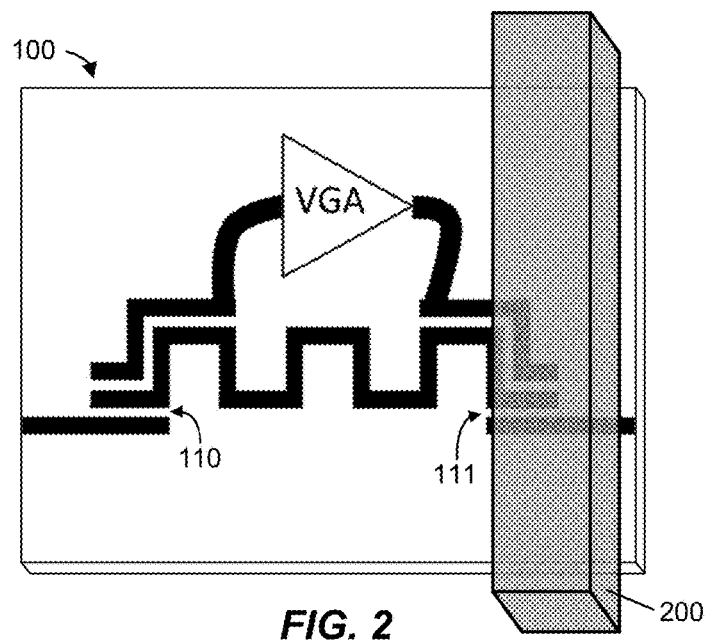
FIG. 2 is a schematic of an example embodiment where a sample has been positioned in relation to a coupling gap of the resonator.
Figure 3:
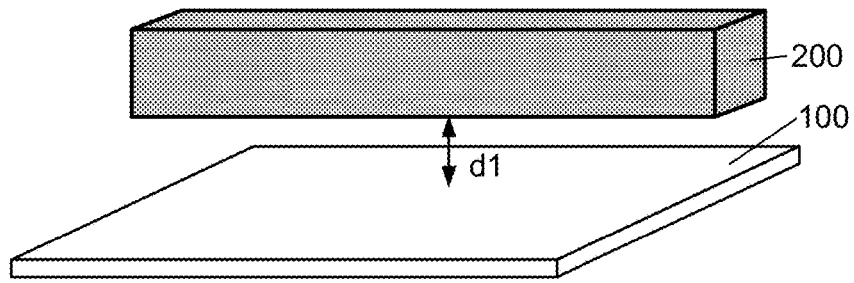
FIG. 3 is a side perspective view showing a distance between a resonator sensor and a sample.

FIG. 2 shows an example embodiment in which a sample 200 is positioned in relation to coupling gap 111 of resonator 100. Sample 200 may be positioned at any suitable distance away from the surface of resonator 100. FIG. 3 is a side view showing an embodiment where sample 200 is positioned at a distance d1 from the surface of resonator 100. In some embodiments, d1 generally has a non-zero value. This is a non-contact sensing configuration. The distance d1 may be a few millimeters (e.g. 0-10 mm), a few centimeters (e.g. 1-10 cm), or even longer depending on the embodiment and the particular application. However, in some embodiments, sample 200 may be in contact with resonator 100, meaning d1 has a value of zero.

The shape and size of sample 200 in FIG. 2, and the orientation and spacing of sample 200 relative to resonator 100 is only an example and thus is not intended to be limiting.

The dielectric constant of a material can be considered as a unique feature or finger print of that material. This feature can be utilized for sensing and determining different materials. Meanwhile, resonance frequency and quality factor of microwave resonators (operating in high frequencies, in range of 300 MHz to 10 GHz), are determined by electrical permittivity in their ambient. Any change or variation in ambient or its electrical property can affect these factors according to the following equations:

$$\varepsilon_{\mathit{eff}} = \frac{\varepsilon_r + 1}{2} + \frac{\varepsilon_r - 1}{2} \frac{1}{\sqrt{1 + 12\frac{d}{W}}} \quad (1)$$

$$Q \propto 1/\sqrt{\varepsilon_{\mathit{eff}}} \quad (2)$$

$$f_0 \propto 1/\sqrt{\varepsilon_{\mathit{eff}}} \quad (3)$$

where $\varepsilon_{\mathit{eff}}$ is the effective permittivity of the ambient near the sensor, $\varepsilon_r$ is the permittivity of the substrate, d is the distance in between the input and signal line and microstrip resonator, W is the width of the microstrip line, Q is the quality factor of the resonator, and $f_0$ is the resonance frequency. As would be understood by a person skilled in the art, the dimensions and relative dimensions (e.g. length, width, etc.) of the lines of the sensor may be chosen to achieve particular sensor parameters.

Substituting one material for another in proximity to the resonator sensor alters the dielectric constant of the surrounded ambient and creates shift in resonance frequency or variation in quality factor of the resonator. All the above equations (1) to (3) are first order equations to demonstrate how ambient variation alters electrical parameters of a microwave resonator.

The resonance frequency ($f_0$) may be determined by the length and width of the resonator loop 108 lines, the feed lines and the material properties of substrate 102 of the resonator. For the passive resonator, the length of the microstrip line plays a critical role in determining the resonance frequency of the system. This resonator is a half-wavelength resonator, thus the total length can be calculated from the following equation:

$$l = \frac{c}{2\sqrt{\varepsilon_{\mathit{eff}}}} \times \frac{1}{f_0} \quad (4)$$

where l is the total length of the resonator, $\varepsilon_{\mathit{eff}}$ is the effective permittivity of the materials in the sensor ambient, c is the velocity of light and $f_0$ is the resonance frequency.

In the active feedback loop of resonator 100, a direct current (DC) feed (not shown) may be provided to the amplifier. The active feedback loop around the main resonator cancels or at least offsets the power loss of the resonator by introducing a negative resistance. This may increase the Q factor of the resonator by several orders of magnitude (e.g. by 3 to 5 orders in some embodiments). In some embodiments, the active feedback loop creates 180 degree phase shift on its output and another 180 degree phase shift is introduced by the passive resonator. In other words, the created phase shift by the resonator loop 108 (a passive meander shape microstrip line) ($\lambda/2$) is summed by the phase shift introduced by amplifier 124, coupling capacitors (e.g. the coupling gap 110 (or 111) between a feed line and resonator loop) and the feedback line 120 length creating a complete cycle required for a positive feedback loop. A constructive (positive) feedback is therefore created around the passive resonator, which compensates the power loss and increases the quality factor. The loss (positive resistance) of the resonator can be partly or completely compensated by the negative resistance provided by the active feedback loop if the gain of the amplifier is driven from the following equation:

$$G = \frac{\sqrt{Q_1 Q_2}}{2} \times \left(\frac{1}{Q_1} + \frac{1}{Q_2} + \frac{1}{Q_u}\right) \quad (5)$$

where G is the gain of the transistor, $Q_1$ and $Q_2$ are the external quality factors due to the gain loading of the input and output ports of the active feedback loop on the passive resonator, and $Q_u$ is the unloaded quality factor of the passive resonator.

An initial quality factor of the resonator, meaning before a lossy medium is presented at the resonator, may be increased by controlling a bias voltage of the amplifier 124. A quality factor factor measurement may be performed by measuring the 3 dB bandwidth of the transmitted power response (S21) and calculating the resonance frequency to bandwidth ratio. An S-parameter (e.g. S21) is a parameter in a scattering matrix, which is a mathematical construct representing how radio frequency (RF) energy propagates through a multi-port network.

A microwave signal of known amplitude and phase, with or without a DC bias, is applied to an input port of the planar resonator. In the present embodiment, this may be feed line 104 (port 1). The input signal may be swept in frequency and the response of the resonator is typically measured using an output port of the resonator, for example line 106 (port 2). In some embodiments, an input port may be used to both apply the stimulus and measure the response by determining the reflected power parameters S11 and S22.

Capacitive coupling may determine the resonator matching, loading and/or bandwidth, which may in turn affect the signal amplitude, resonance frequency and/or the quality factor. For measurements of one or more parameters of a sample under investigation, a shift in one or both of resonance frequency $f_0$ and quality factor Q may be monitored. Both the real and imaginary parts of the electrical permittivity (and therefore the complex conductivity) of the material in the coupling gap may be extracted by measuring the resonance frequency and the quality factor of a microwave signal. These parameters may be simply extractable from S-parameters of the microwave resonator. For isotropic materials, at least two of the following four quantities may be measured to completely determine the complex permittivity: amplitude, phase, resonance frequency and quality factor.

S parameters of the resonator may be directly measured using a vector network analyzer or other test equipment. Alternatively, the resonator with an active regenerative feedback loop may be used as the core resonator for conventional oscillating circuits such as a voltage-controlled oscillator (VCO) or a phase-locked loop (PLL) circuit and their output frequency is measured as the output indictor down converting for signal processing.

Enhanced Field of View

The enhanced field of view of a resonator in some embodiments is now described. In resonator 100 comprising the active feedback loop, a constructive signal increases the electric field amplitude around the resonator by compensating at least part of the loss of the resonator and the medium with negative resistance at its ports. Increasing the quality factor also increases the depth of the penetration of the electric field since it creates a stronger field which occupies a bigger volume. Depth of electric field penetration also depends on the quality factor of the microwave resonator according to the following equations:

$$\frac{\Delta f_0}{f_0} \propto -\frac{\mathrm{Re}\left(\frac{P}{E^*}\right)}{2V_{\mathit{eff}}} \quad (6)$$

$$\Delta\left(\frac{1}{Q}\right) \propto -\frac{\mathrm{Im}\left(\frac{P}{E^*}\right)}{V_{\mathit{eff}}} \quad (7)$$

where $f_0$ is (the center frequency), $\Delta f_0$ is (bandwidth between the −3 dB frequencies), P is the induced electric dipole moment, $E^*$ is electric field, $V_{\mathit{eff}}$ is effective volume occupied by electric energy, and Re( ) and Im( ) represent the real and imaginary components, respectively.

Furthermore, the presence of a sample in a region with a high electric field concentration affects the resonance frequency as well as the quality factor. This effect can be described using perturbation analysis as shown in the following equations:

$$\frac{\Delta f_0}{f_0} \approx -\frac{\Delta U}{U_{tot}}, \quad (8)$$

and $$Q \approx \frac{2\pi f_0 U_{tot}}{\text{time averaged power dissipation}}$$

where $\Delta U$ is the electromagnetic energy variation regarding to presence of a sample in the resonator ambient, $U_{tot}$ is the time averaged stored electromagnetic energy in the resonator and is equal to $U_{tot} = \frac{1}{2}\varepsilon_0 \int E^2 dV$, and V is the volume occupied by electric energy. Based on this equation, it is expected that by improving the quality factor, the $U_{tot}$ and thus the total electric field and the occupied volume by field increases. Consequently, the field of view of the sensor maybe enhanced, which may allow for improved non-contact measurement and sensing.

Increasing the quality factor of the resonator may also affect the resolution and the minimum detectable frequency shift as described in the following equation:

$$\Delta f_{min} = \frac{3\sqrt{3} \, f_0}{4 A_{omax} Q} \times \Delta A_{min} \quad (9)$$

where $f_0$ is the resonance frequency, $A_{omax}$ is the maximum amplitude which occurs at the resonance frequency, Q is the quality factor of the resonator, and $\Delta A_{min}$ is the minimum variation in resonance profile amplitude, which is considered three times the amplitude of the electric white-noise.

Increasing the quality factor not only affects the field of view for the sensor but also increases the resolution and minimum detectable permittivity according to the following equation:

$$|\Delta \varepsilon_{min}| = \frac{9\varepsilon\sqrt{3}}{2V_{omax}Q} \times \sqrt{4kTBR} \qquad (10)$$

where $\varepsilon$ is permittivity of the surrounding ambient, $|\Delta\varepsilon_{min}|$ is minimum detectable permittivity change, $V_{omax}$ is maximum amplitude of the resonance profile, k is Boltzmann constant, T is temperature in Kelvin, B is frequency bandwidth of the resonance profile, and R is physical resistance of the resonator sensor.

Again, an enhanced field of view obtained by using a planar microwave resonator comprising an active feedback loop may be utilized for achieving higher resolution sensing. Furthermore, an enhanced field of view of the resonator may allow the sample being investigated to be located farther away from the resonator rather than being in near or actual contact with the resonator.

Figure 4:
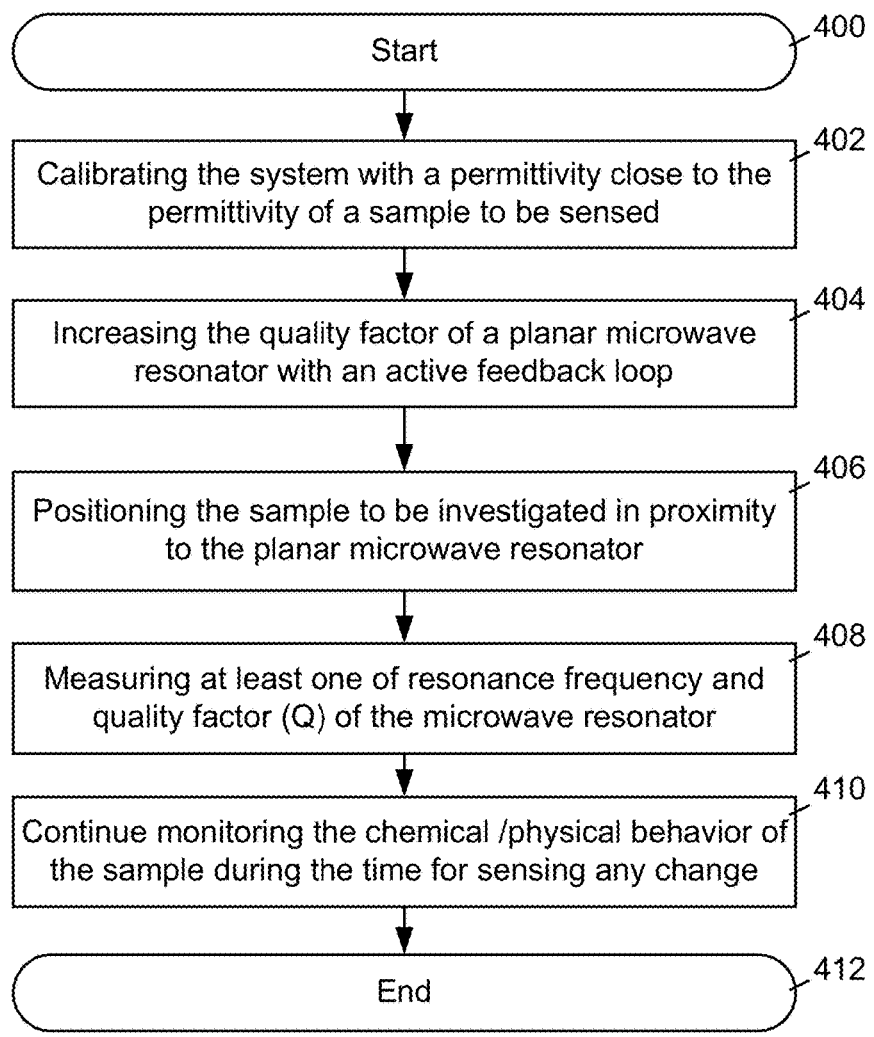
FIG. 4 is an example process for increasing the quality factor of a resonator in a sensing application.

An example process according to the present disclosure is shown in FIG. 4. The process starts at block 400 and proceeds to block 402 where the system may be calibrated with a permittivity close to the permittivity of a sample to be sensed. The process proceeds to block 404 where the quality factor of a planar microwave resonator is increased with an active feedback loop. This may involve adjusting a direct current (DC) bias voltage of an amplifier in the active feedback loop to obtain a particular quality factor. The process proceeds to block 406 where a sample to be investigated is positioned in proximity to the planar microwave resonator. Alternatively, the resonator may be positioned in proximity to the sample, or the resonator may already be positioned in this way relative to the sample. In some embodiments, if the sample is too far away from the sensor so that its variation is not detectable, the amplifier gain in the feedback loop may be adjusted (e.g. by adjusting a DC bias) to enhance the quality factor, and hence the field of the view and the resolution of the sensor.

The process proceeds to block 408 where at least one of resonance frequency and quality factor (Q) of the microwave resonator is measured in response to the application of a resonator signal to the sample. One or both of the real and imaginary parts of the electrical permittivity (and therefore the complex conductivity) of the sample may be extracted by measuring one or more of the amplitude, frequency and the quality factor of the microwave signal. In some embodiments, these parameters may be simply extractable from S-parameters of the scattering matrix for the microwave resonator.

The process proceeds to block 410 where sensing or other monitoring of the physical or chemical properties of the sample continues over a time period. The process proceeds to block 412 and ends.

Compensation of Signal Loss

The compensation of a resonator signal loss in a lossy medium in some embodiments is now described. A resonator comprising an active feedback loop may be initially configured to have a high initial quality factor before a lossy sample or medium is presented within the field of view of the resonator. The initial quality factor may be set by controlling a bias voltage of the amplifier 124 in the active feedback loop. A lossy sample or medium, such as aquatic environment, may then be positioned at or near the resonator. The higher permittivity of the lossy sample causes energy of the resonator to be absorbed by the sample. This energy is therefore lost in the sample, thereby degrading the resonator signal and reducing the quality factor of the resonator. To compensate or adapt for at least some of this loss, the amplifier gain in the active feedback loop may be adjusted again to retrieve the resonator signal and increase the quality factor above its reduced level. Once more, the amplifier gain (and quality factor) may be adjusted by modifying the bias voltage of the amplifier.

A planar microwave resonator with a regenerative active feedback loop may be used to perform high resolution sensing and its DC bias may be used to adjust the dynamic range of the resonator. The dynamic range is the range of the effective permittivity that can be sensed in high resolutions by the sensor. For instance, if the sensor is adjusted for a high quality factor Q and high resolution sensing using a secondary layer or material with low complex permittivity, the signal may be dimmed by changing the secondary layer material to a lossy one or to a material having a high complex permittivity. Adjusting the DC bias may enable high resolution sensing in the latter material. In another words, adjusting the DC bias may extend the dynamic range to the new material.

Figure 5:
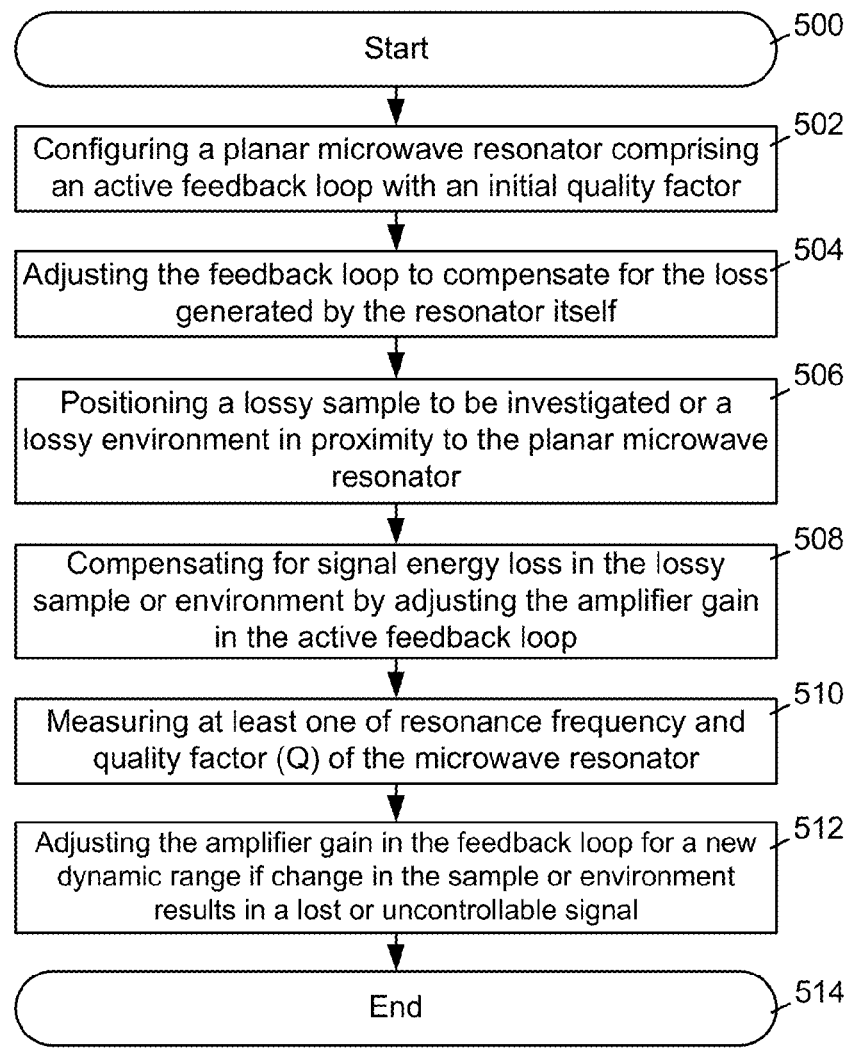
FIG. 5 is an example process for compensating for energy loss of a resonator sensor in a lossy sample or environment.

Another example process according to the present disclosure is shown in FIG. 5. The process starts at block 500 and proceeds to block 502 where a planar microwave resonator comprising an active feedback loop is configured with an initial quality factor. The process proceeds to block 504 where the feedback loop may be adjusted to compensate for any signal loss generated or caused by the resonator itself. Adjusting the feedback loop may include adjusting a gain level of an amplifier, for example by adjusting a bias voltage. The process proceeds to block 506 where a lossy sample to be investigated or a lossy environment is positioned in proximity to the resonator. In some embodiments, a sample to be investigated may be located within the lossy environment. Accordingly, in these embodiments, the microwave signal must propagate through the lossy environment to reach the sample.

The process proceeds to block 508 where signal energy loss in the lossy sample or environment is at least partially compensated by adjusting the amplifier gain in the active feedback loop. The process proceeds to block 510 where at least one of resonance frequency and quality factor (Q) of the microwave resonator is measured.

The process then proceeds to block 512 where the amplifier gain in the feedback loop may be adjusted for a new dynamic range if change in the sample or environment results in a lost or uncontrollable signal. The process then proceeds to block 514 and ends.

In some embodiments, a planar microwave resonator may be able to achieve a quality factor of at least 1000 when in proximity to a lossy sample or a lossy medium. In some embodiments, the resonator may be able to achieve a quality factor of at least 5000 when in proximity to a lossy sample or medium. In some embodiments, the resonator may be able to achieve a quality factor of at least 10,000 or higher when in proximity to a lossy sample or medium.

In addition, in some embodiments, a planar microwave resonator may be selectively operated at two or more resonance frequencies for varied sensing applications. For example, a resonator may be operated at a first resonance frequency, and subsequently at a second resonance frequency. The sensor can be designed with multi loop and multiple resonance frequencies with multiple hot spots or coupling capacitors. Each of the hot spots may be integrated with a different secondary layer that is selective to a different gas or liquid. This may enable high resolution selective sensing using microwave sensors.

Furthermore, in some embodiments, a planar microwave resonator may be operated at one or more high harmonic frequencies to provide additional selectivity in sensing applications.

A planar microwave resonator configured with an active feedback loop according to the present disclosure may be used in various applications. The applications mentioned and described herein are provided as examples only, and are not meant to be limiting.

In one application, a planar microwave resonator with an active feedback loop may be used in noncontact material classification and detection in liquid water (as a lossy environment) or in air. One example type of noncontact sensing is the sensing and characterization of bead sizes. The size of beads and the compactness of the beads may be sensed and measured even when the sizes of the beads fall within a small range (e.g. the beads are of a similar size).

Adsorbents are porous materials widely used in different processes including gas adsorptive separation, catalysis, and pollutants abatement systems. These materials can be used in different forms (granular, bead, wires, tubes and powder) and configurations (packed and fluidized columns). Depending on the column and the adsorbent dimensions and the conditions (nano, micro or milli) applied during the process (e.g. fluid flow rate), they can have different porosities (void fractions).

In some embodiments, a container containing a material, such as beads, may be positioned proximate a planar microwave resonator sensor having an active feedback loop. They can be used also as a secondary layer to absorb or select specific materials.

In another application, a planar microwave resonator with an active feedback loop may be used in noncontact liquid to liquid interface sensing and detection. Variations in one or more parameters of the sensor, such as resonance frequency or quality factor, may be used to detect such a liquid to liquid interface. Liquid to liquid interfaces include but are not limited to water-olive oil, water—olive oil—ethanol, and rag layer samples. This type of sensing has various applications including in oil sands processing.

The rag layer is an undesirable mixture of water, fine solids and dispersed oil formed at the water-oil interface during the settling stages in the froth treatment of oil sands. Detecting the exact location of rag layer is important is assuring the quality of produced oil as well preventing the loss of bitumen to the tailing. Once entered into the oil stream, water and fine solids can contaminate the produced oil and may cause fouling and corrosion problems in the downstream processes. Therefore, a reliable non-contact sensor that can detect interfaces is of great interest.

Experiment 1

Figure 6:
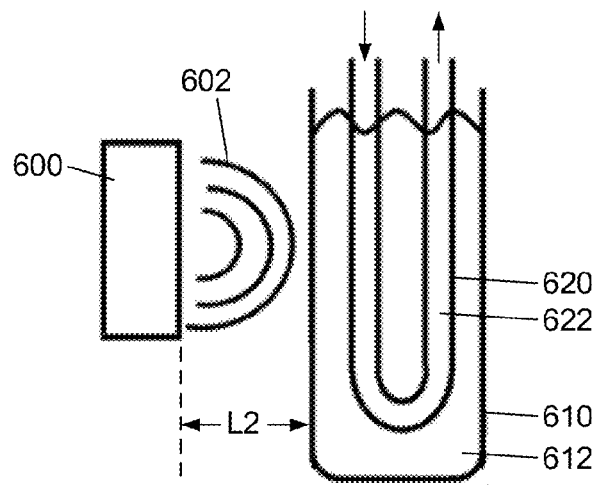
FIG. 6 is a side view of a setup for liquid sensing using a planar microwave resonator sensor having an active feedback loop.

A first experiment involved non-contact liquid sensing in an aquatic environment using an active, feedback loop assisted, planar microwave resonator. FIG. 6 is a schematic representing the setup used in the experiment comprising a sensor 600 comprising a planar microwave resonator, and a deionized water-filled container 610 located a distance L2 from sensor 600. Lines 602 represent an electric field generated by sensor 600. A portion of tube 620 is positioned in the water within container 610.

The core of sensor 600 is a passive meander-shaped resonator which is assisted with a feedback loop employing a low noise, high gain transistor from California Eastern Laboratories (CEL) as an amplifier. The resonator is fabricated on a printed circuit board (PCB) from Rogers corporation (5880) with a thickness of 0.79 mm and a dielectric constant of 2.2+/−0.2. Substrate surfaces are covered with a thin layer of copper with conductivity of $5.8 \times 10^7$ Sm$^{-1}$ and thickness of 37 um. The loss factor of the substrate is 0.0003, which is low and thus suitable for a range of operation frequency.

Figure 7:
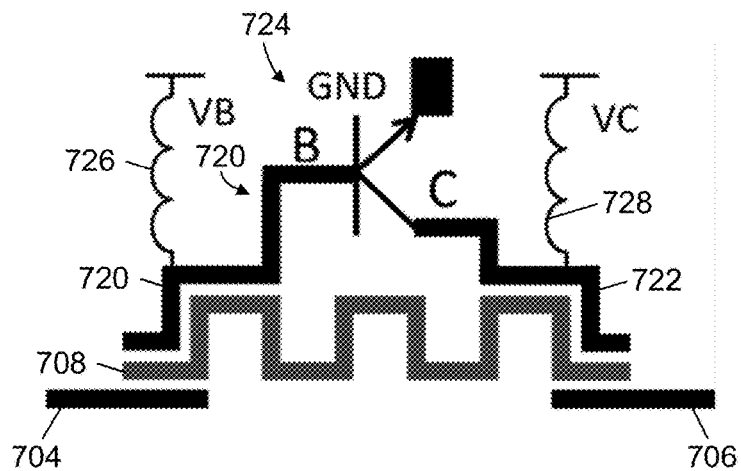
FIG. 7 is a schematic of a microwave resonator sensor used in an experiment having the setup shown in FIG. 6.

FIG. 7 is a schematic of resonator 600 comprising first and second feed lines 704 and 706 (e.g. port 1 and port 2), respectively, resonator loop 708, and an active feedback loop 720 comprising feedback lines 721 and 722, and a variable gain amplifier 724. Two 18 μH inductors 726, 728 were used as the direct current (DC) feed to transistor 724. The collector voltage (VC) of the transistor was set to 8V and the base voltage (VB) was kept variable to achieve the highest quality factor in different conditions. Having the active feedback loop around the main resonator canceled the power loss of the resonator by introducing a negative resistance, and increased the quality factor by 3 to 4 orders of magnitude.

Figure 8:
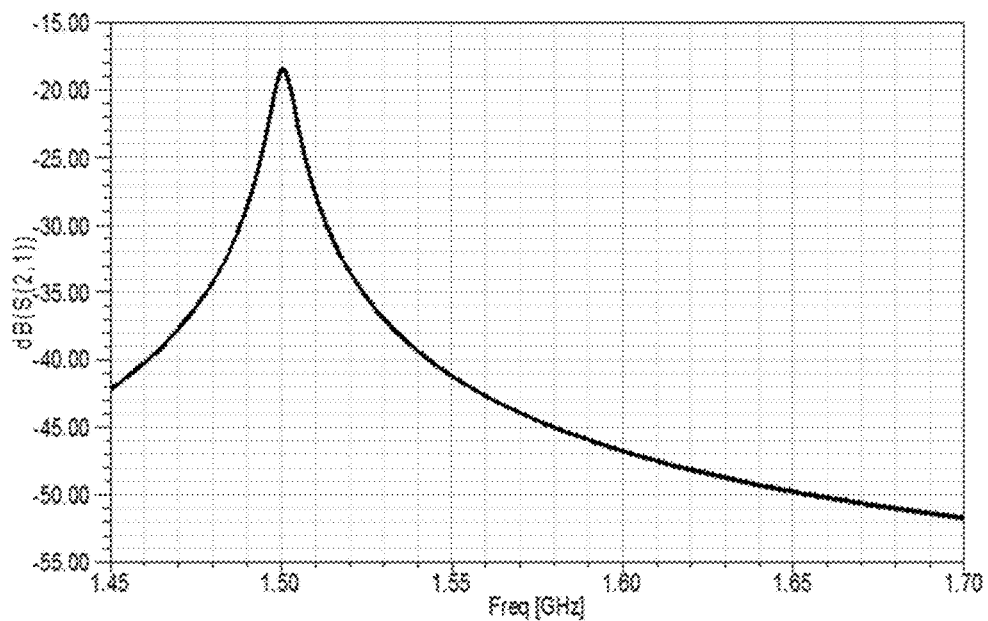
FIG. 8 is a graph of passive sensor scattering parameter (S21) simulation results of the sensor of FIG. 6.

FIG. 8 shows passive sensor S21 parameter simulation results performed using a High Frequency Structure Simulator (HFSS). The results demonstrated that the initial design of passive resonator was working correctly and had the expected performance.

Figure 9:
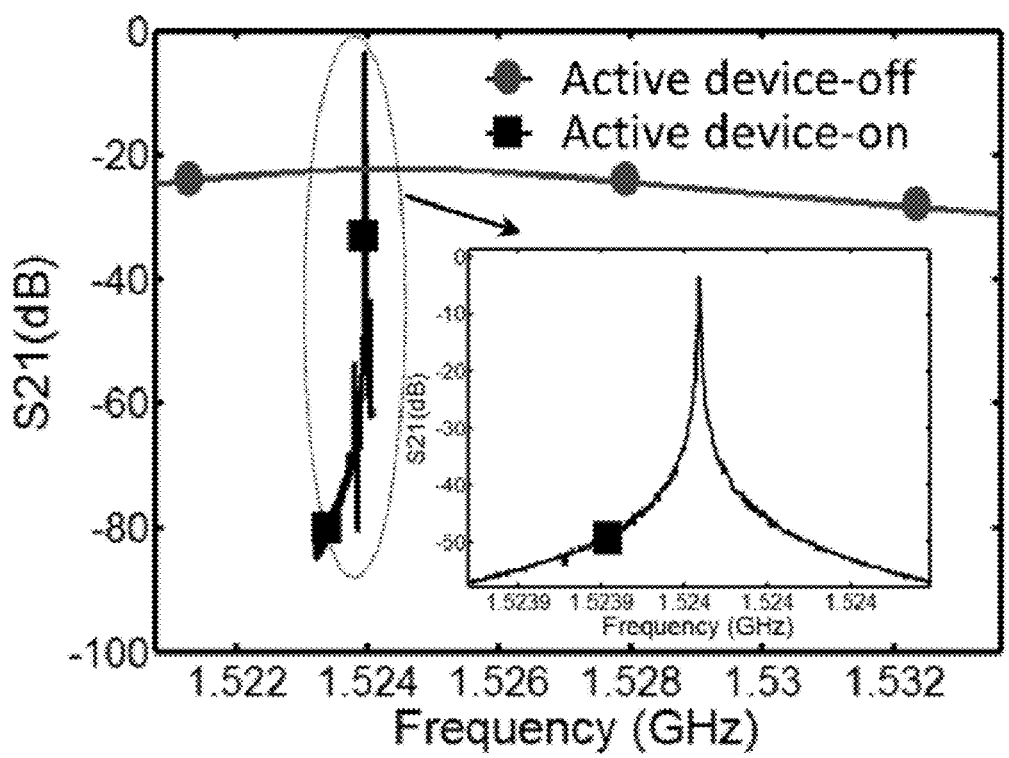
FIG. 9 is a graph comparing the measured resonance profiles (S21 parameter) for off and on states of the active feedback loop of the sensor of FIG. 6.

FIG. 9 shows a comparison of the measured resonance profiles (S21 parameter) for off and on states of the active feedback loop. The inset shows the resonance profile for the active device on state in finer resolution in the approximate range of 1.5239 to 1.5240 GHz. The initial quality factor of the resonator was 200, which was increased to 800,000 by modifying the bias voltage of the transistor. The quality factor measurement was performed by measuring the 3 dB bandwidth of the transmitted power response (S21) and calculating the resonance frequency to bandwidth ratio. For both on and off states, the resonance frequency was around 1.52 GHz. The amplitude of the S21 parameter in the off state of the active device was approximately −21 dB (as shown by the active device-off line), and this amplitude increased to approximately −1.2 dB (as shown by the active device-on line) since the active feedback loop provided gain as well as at least partly compensated for the dissipation loss of the microwave signal in the water in container 610.

In addition, field measurements around the resonator were performed with an EMSCAN™ device. The sensor was placed in the center of plate of the electric-field scanner and the electromagnetic field was measured for both on and off states of the active feedback loop. With the feedback loop inactive, the initial quality factor was determined to be approximately 200. With the feedback loop turned on, the quality factor was determined to be approximately 200,000. Increasing the quality factor of the resonator increased the field distribution and the depth of electric field penetration around the resonator. The resulting high depth of penetrated field enables sample measurements from long distances from the resonator, for example at least up to 12 cm or more.

Figure 10:
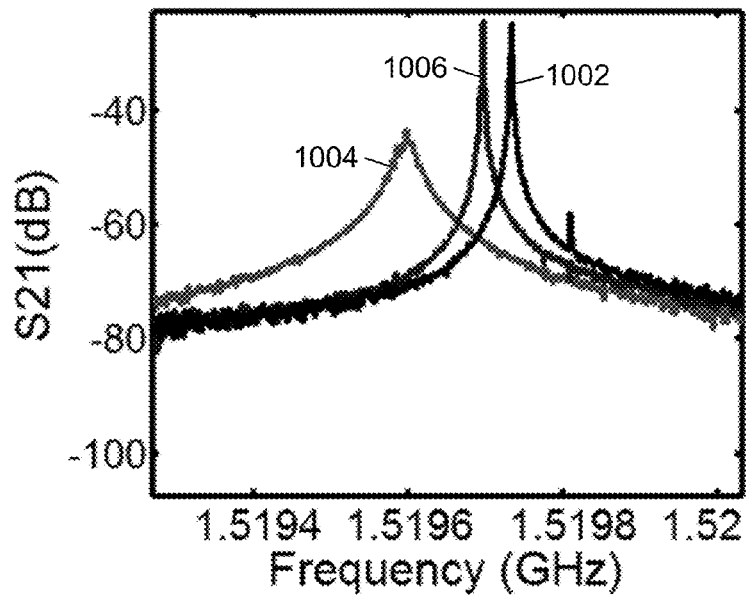
FIG. 10 is a graph of various S21 parameter measurements of the sensor of FIG. 6.

FIG. 10 shows various S21 parameter measurements of the active resonator 600. Line 1002 represents the S21 parameter measurements of the active resonator before water-filled container 610 is positioned in proximity to the resonator 600 with the amplifier bias voltage (VB) set at 0.67 V. The S21-parameter of resonator 600 without any sample had a quality factor of approximately 500,000. When the water-filled container 610 was positioned in proximity to resonator 600, the quality factor of the resonator dropped to approximately 35,000, as indicated by line 1004. The quality factor was then increased by adjusting the DC bias voltage (VB) of amplifier 724 from 0.670 V to 0.692 V, which raised the quality factor up again to approximately 450,000 in the presence of water-filled container 610. The resonance frequency and quality factor may then have been used as a base line for further measurements of the liquid(s) 622 inside the submerged tube 620 in water-filled container 610. Accordingly, this demonstrates that high quality factor sensing in the presence of an aquatic environment (or other lossy sample or environment) is possible.

To demonstrate the noncontact operation of sensor 600, and its high sensitivity to different liquids located within an aquatic environment (e.g. within tube 620), two sets of measurements were performed for different distances of L2=5 cm and L2=8 cm (L2 is indicated in FIG. 6). For each different liquid, a measuring duration of 5 minutes was considered to demonstrate the stability of resonator 600 and the robustness in the measured parameters while the environment temperature was kept constant at room temperature of 24 degrees C. Container 610 having an inner diameter of 2.5 cm was filled with deionized water, and smaller tube 620 having an inner diameter of 4 mm was left empty (air). The quality factor of resonator 600 was measured to be approximately 450,000 in the presense of water-filled container 610 and the resonance frequency was measured at approximately 1.52 GHz. Different liquids were injected into tube 620 one at a time and measurements were performed. The liquids were ethanol (E), methanol (M), isopropanol (I), aceton(A), and water (W). Between each injection, air was used to purge the inside of tube 620 for 5 minutes to return the measured parameters to the base line of empty tube 620.

Figure 11A:
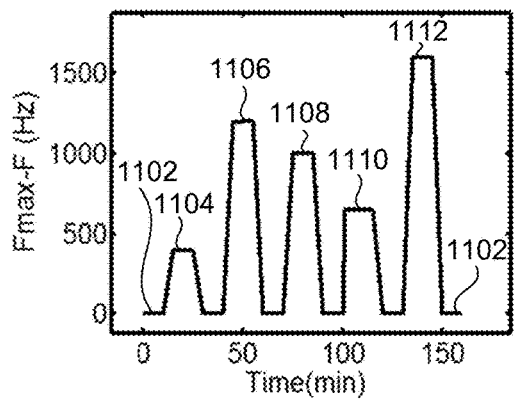
FIGS. 11A and 11B are graphs showing time domain measurements of the resonance frequency shift of resonator of FIG. 6 for different liquids in the tube.
Figure 11B:
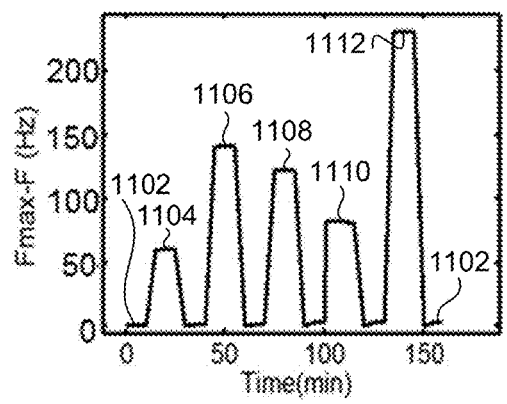

Scattering parameter measurements were performed using a network analyzer from Agilent™ (E8362) and a bias voltage was applied using a function generator with an accuracy of 0.1 mV from Rigol company. Data acquisition was automatically performed utilizing Labview™ and the data was processed in MATLAB™. According to the measured results, having the sample closer to the sensor created larger shifts in the resonance frequency of resonator 600. Moving the sample farther away from the resonator resulted in smaller shifts in the resonance frequency. However, since the sensor had a very high quality factor, these smaller shifts in resonance frequency were still detectable and distinguishable. In some embodiments, variations as small as 10 parts per billion may be measured, and possibility as low as 0.1 part per billion ($10^{-10}$) (and even lower) in resonance frequency, quality factor, or amplitude may be detectable. FIGS. 11A and 11B show the time domain measurement of resonance frequency shift of resonator 600 for the different liquids where water-filled container 610 was positioned at two different distances away from resonator 600, namely L2=5 cm and L2=8 cm, respectively. The resonance frequency shift for each of the liquids are labeled in FIGS. 11A and 11B as follows: ethanol 1104, methanol 1106, isopropanol 1108, aceton 1110, and water 1112. Air is labeled with reference number 1102.

Therefore experiment 1 demonstrates high quality factor sensing in the presence of an aquatic environment (or other lossy sample or environment). The DC voltage and the amplifier gain may be adjusted to compensate for the secondary medium (water) and to perform high resolution sensing. Due to a high quality factor of the resonator, smaller shifts in resonance frequency caused by different samples (e.g. the different liquid samples inside the inner tube in the water container) were detectable and distinguishable in the lossy environment.

Experiment 2

A second experiment using an active, feedback loop assisted, planar microwave resonator was conducted. A first part of the experiment demonstrated high sensitivity sensing of different types of liquids (such as methanol, ethanol, isopropanol, water, and water based solutions). The presence of the different liquids was clearly distinguishable by the sensor. A second part of the experiment demonstrated high sensitivity sensing of small concentration variations in a liquid. The variations in concentration were distinguishable to the sensor.

Figure 12:
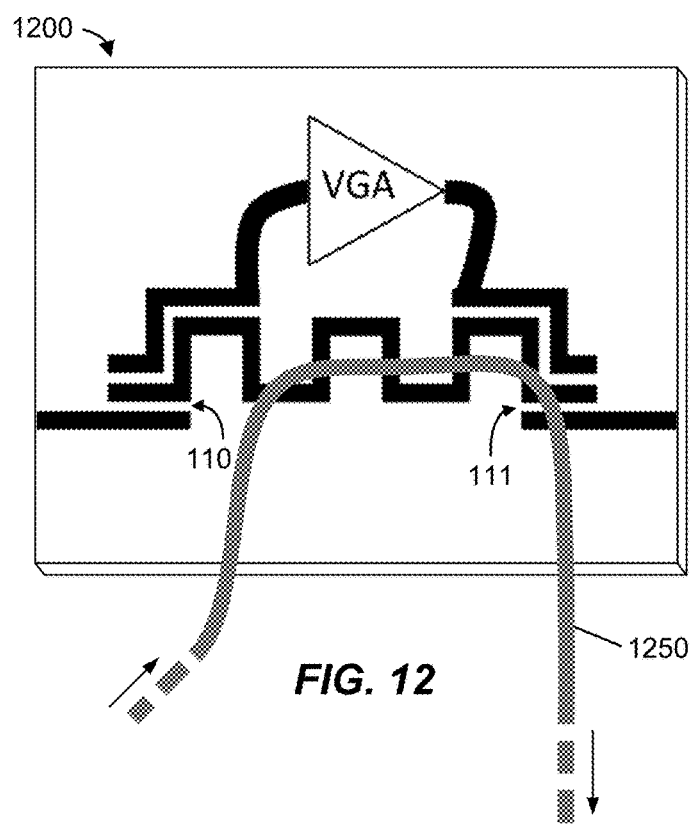
FIG. 12 is a schematic of a microwave resonator sensor and a microfluidic tube for use in a liquid sensing application.

FIG. 12 shows a schematic of the setup of the second experiment. A planar microwave resonator sensor 1200 similar to the resonator described with reference to FIG. 1 was used. A microfluidic tube 1250 having inner diameter of 0.4 mm was fixed on the surface of sensor 1200 with a strong scotch tape such that part of tube 1250 was aligned with the resonator and the coupling gap 111 of the resonator. The flow path of the fluid in microfluidic tube 1250 was chosen to coincide with areas of high field intensity of the resonator in order to maximize interaction of the fluid with the microwaves. Arrows indicate the direction that liquid was passed through tube 1250. Resonator 1200 was operated at 1.4 GHz with a passive quality factor of 200. Resonator was assisted by an active feedback loop, which increased the quality factor to 22,000 for the bare resonator with tube 1250 positioned proximate its surface.

Resonator 1200 was implemented on a low dielectric-loss substrate 5880 from Rogers Corporation. Both sides of the substrate were initially covered by 35 μm copper layers with a conductivity of $5.8 \times 10^7$ Sm$^{-1}$; the dielectric constant and the loss tangent of the substrate were 2.2+/−0.02 and 0.0003, respectively. A NE680 transistor amplifier from California Eastern Laboratories (CEL), which is a low noise, high gain, and low cost transistor with a typical cut-off frequency of 10 GHz at 10 mA bias current, was used as an active amplifier in the feedback loop. High frequency high quality inductors (18 nH) were used as direct current (DC) bias couplers to provide bias for the transistor.

Figure 13A:
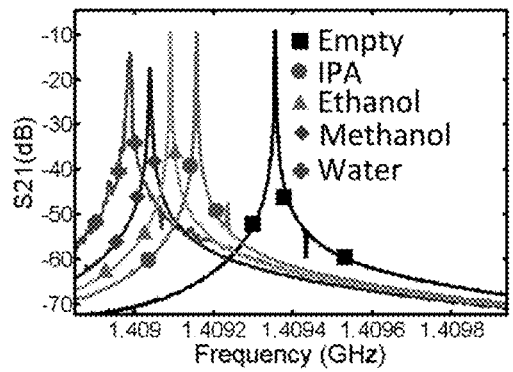
FIG. 13A is a graph showing results of S-parameter measurements for different liquids inside the microfluidic tube while the active feedback loop was in operation.
Figure 13B:
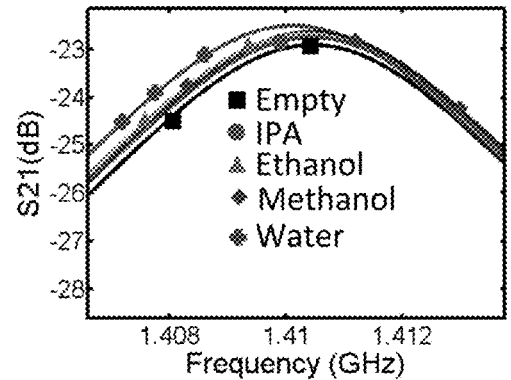
FIG. 13B is a graph showing results of S-parameter measurements for different liquids inside the microfluidic tube while the active feedback loop was turned off.

To experimentally verify sensor 1200, two sets of measurements are presented: different liquid sensing, and concentration detection. For the first test, tube 1250 was filled by five different liquids, namely methanol ($\varepsilon'$=30, $\varepsilon''$=8), ethanol ($\varepsilon'$=24, $\varepsilon''$=12), isopropanol ("IPA", $\varepsilon'$=17.9, $\varepsilon''$=17.5), and deionized (DI) water ($\varepsilon'$=80, $\varepsilon''$=3.7). The S21 profile of sensor 1250 was measured using a vector network analyzer (VNA-E8362) from Agilent. The results show a quality factor of 22,000 for the bare sensor, meaning tube 1250 is present at the sensor but there was liquid in tube 1250. FIG. 13A shows the results of S-parameter measurements for the different liquids inside microfluidic tube 1250 while the active feedback loop was in operation. FIG. 13B shows the results of S-parameter measurements for the same liquids inside tube 1250 while the active feedback loop is was turned off. A very clear and distinct difference was observed between different liquids when the active feedback loop was utilized (FIG. 13A) compared to when the resonator was operated in passive mode, meaning when the active feedback loop was off (FIG. 13B).

The difference in permittivity ($\varepsilon'$) and in the loss ($\varepsilon''$) created differences between the S-parameters of these liquid samples. The difference in electromagnetic properties of each of the liquids in tube 1250 is reflected in the frequency variation of the resonator 1200, as shown in FIG. 13A.

The high quality factor of sensor 1200 also allows for high-resolution measurement inside a secondary material such as a small tube and performing experiments such as concentration tests. Therefore, in the second part of the experiment, sensor 1200 was used for concentration measurements of soluble materials in solvents, namely for potassium hydroxide (KOH) in water.

Figure 14A:
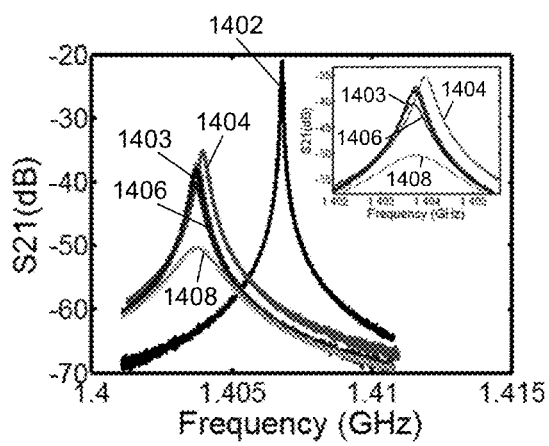
FIG. 14A is a graph showing S21 parameter measurements for the bare resonator (tube present but no liquid inside) and for different concentrations of KOH in water in the tube.
Figure 14B:
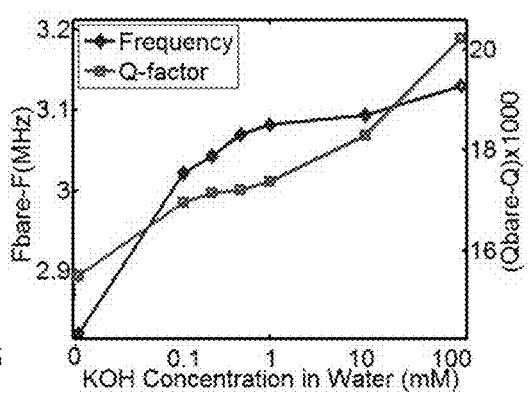
FIG. 14B is a graph showing measurements of resonance frequency and quality factor of the resonator sensor for KOH concentration of 0.125 mM to 100 mM diluted in water.

FIG. 14A shows S21 parameter measurements for the bare resonator (tube 1250 present, but no liquid inside) and for different concentrations of KOH in water in tube 1250. Specifically, line 1402 represents the results of the resonator with no tube present, line 1403 with tube 1250 present but empty, line 1404 with KOH having a concentration of 0.125 mM, line 1406 with KOH having a concentration of 10 mM, and line 1408 with KOH having a concentration of 100 mM. FIG. 14A also contains an inset showing part of the graph in more detail FIG. 14B shows resonance frequency and quality factor of sensor 1200 for KOH concentration of 0.125 mM to 100 mM diluted in water. It was shown that increasing the concentration of the analyte reduces the resonance frequency and enables the detection of various concentrations. In addition, the quality factor also decreases as the concentration is increased. Sensor 1200 enabled significantly lower concentration detection compared to previous microwave sensors.

Experiment 3

Figure 15:
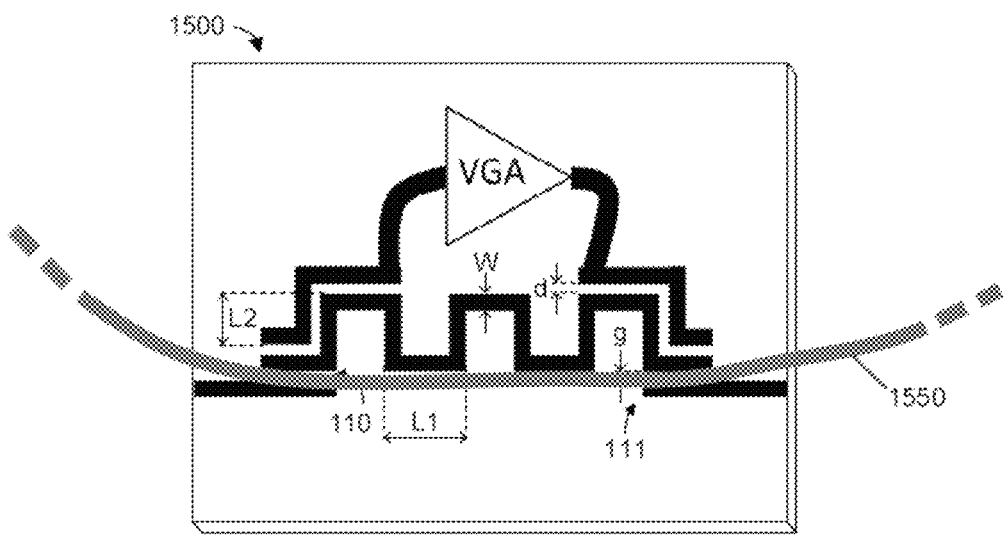
FIG. 15 is a schematic of a microwave resonator sensor and a tube for use in a liquid sensing application.
Figure 16:
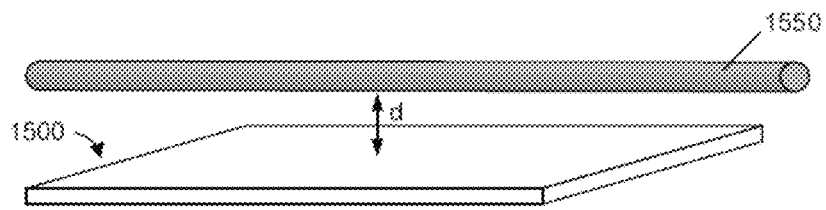
FIG. 16 is a side perspective view showing a distance between a resonator sensor and a tube.

A third experiment using an active, feedback loop assisted, planar microwave resonator demonstrated a quality factor improvement of about 5 orders of magnitude and the enabling of non-contact distant liquid sensing. A tube was placed at 1 cm from the surface of the sensor, different liquids were passed through the tube, and measurements were conducted. The liquids used were isopropanol alcohol (IPA), methanol, ethanol and acetone. FIG. 15 shows the setup of the experiment, comprising planar microwave resonator sensor 1500 and tube 1550. The distances labeled in FIG. 15 had the following values: L1=9 mm, L2=9 mm, W=2.4 mm, d=0.4 mm, and g=1 mm. FIG. 16 shows the spacing having a distance 'd' between tube 1550 and resonator 1500, which in this experiment was set at 1 cm.

To accurately predict the response of the entire sensor, some simulations were performed. S-parameters from HFSS were extracted and imported to Advance Design System (ADS) software, where it was integrated with active circuitry. A transistor model was obtained from the datasheet and implemented in ADS. In the active feedback loop, a low-noise, low-power, microwave transistor, NE68033, from California Eastern Laboratories (CEL), with a unity-gain current frequency (fT) of 10 GHz, was used. The bias voltage was provided through two microwave inductors (22 nH) to the base and collector of the transistor while the emitter was grounded. In such configurations, the bias voltage of the base of the transistor was used to adjust the gain of the active feedback loop.

Figure 17A:
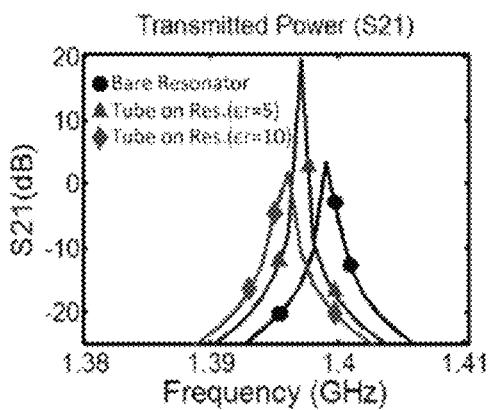
Figure 17B:
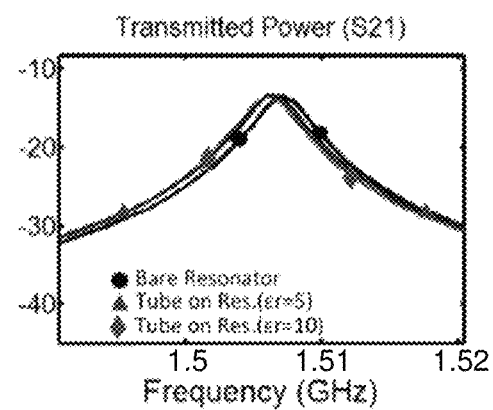
FIG. 17B is a graph showing S21 parameter simulation results for the resonator sensor of FIG. 15 with the tube both present and not present, and the active feedback loop turned off.

S21 simulations over a 30 MHz frequency span were performed for the bare resonator (no tube present), for a tube having a permittivity of 5 present, and for a tube having a permittivity of 10 present. The results of the simulation with and without the active feedback loop in operation are shown in FIGS. 17A and 17B, respectively.

According to the simulation results, the quality factor of the passive resonator was 240, which was improved to 3000 using a bias voltage of 0.72 V for the amplifier. It was clearly observed that having a tube at a distance of 1 cm from the surface of the resonator does not create a distinguishable variation in the passive resonator (e.g. FIG. 17B) but was easily detected by the same resonator while the active feedback was is in the on state (e.g. FIG. 17A).

The simulations demonstrated that increasing the quality factor decreases the minimum detectable permittivity and enables the device to sense very small variations in the ambient permittivity, which in return enables the distant non-contact liquid sensing.

The actual resonator sensor used in the experiment was implemented on a substrate from Rogers Corporation (5880). The substrate had a relative permittivity of 2.2 with a loss factor of 0.0003 and a thickness of 0.79 mm. Both sides of the substrate were covered by copper of thickness and conductivity of 0.035 mm and 5.8 MS/m, respectively. A wet etching PCB development technique was performed to implement the core ring resonator. The active feedback loop was then assembled manually.

The experiment results are now discussed. Initial measurement of the S21 parameter for the bare resonator with active loop in the on-state, using PNA (E8362B) from Agilent, demonstrated a quality factor of approximately 215,000 at resonant frequency of 1.5 GHz with a bias voltage of 0.702 V. The quality factor was measured based on the ratio of the resonant frequency to the 3 dB bandwidth of the resonance profile. Table 1 provides the performance of the resonator in the two states, presenting the amplitude (Amp), resonant frequency (fr) and quality factor (Q), while comparing the measurement results with simulations:

TABLE 1

Measured parameters and comparison between simulation and measurement of the sensor

| Feedback state | Amp (dB) | Q | Fr (GHz) |
| --- | --- | --- | --- |
| Off (measured) | −22.9 | 210 | 1.501 |
| Off (Simulation) | −16.2 | 250 | 1.508 |
| On (measured) | 1.08 | 200,000 | 1.499 |
| On (Simulation) | 0 | 3000 | 1.398 |

The difference in the quality factor for the measurement and simulation is mostly originated from the limited number of points that have been used for the FEM simulation to avoid the long simulation time.

FIG. 18 shows the measured S21 for the active and passive resonator with and without tube 1550 positioned at a distance of approximately 1 cm from resonator 1500. Specifically, line 1802 represents S21 measurements for the resonator operating in passive mode (feedback loop turned off) without the pipe being present. Line 1804 represents S21 measurements for the resonator operating in passive mode with the pipe being present. Line 1806 represents S21 measurements for the resonator operating in active mode (feedback loop turned on) without the pipe being present. Line 1806 represents S21 measurements for the resonator operating in active mode with the pipe being present.

FIG. 18 also contains an inset showing the region of the graph indicated by the dashed oval in more detail.

The performance of resonator 1500 in a non-contact and distant liquid sensing application, isopropanol alcohol (IPA), methanol, ethanol and acetone were used as target liquids, which were each separately passed through tube 1550. Measurements were made using resonator 1500 while operating in both passive mode and in active mode.

The result of the S21 measurements are shown in FIG. 19A (passive mode) and FIG. 19B (active mode). In the passive mode, the difference of the resonances of the resonator due to the different liquids was not clearly distinguishable, as shown in FIG. 19A. In contrast, the results from the active mode are very clear and distinguishable, as shown in FIG. 19B. All measurements were performed at least five times for each target liquid to reduce the effect of noise and measurement-error.

This experiment demonstrated non-contact distant liquid sensing using a planar microwave resonator having an active feedback loop.

Secondary Layer or Material

In another aspect, the present disclosure is directed to a planar microwave resonator with an active regenerative feedback loop comprising a secondary layer defining a sensing interface.

In some embodiments, the secondary layer may facilitate the sensing by exposing it to another substance (e.g. a gas, liquid, or solid) or to a physical stimulation (e.g. light, other electromagnetic radiation, heat, vibration, etc.), which changes the effective permittivity and conductivity of the secondary layer. The substance or physical stimulation may be referred to herein simply as a sample. Thus the sample being investigated interacts with the secondary layer. Since the complex permittivity of the secondary layer can vary when exposed the sample, the interaction phenomenon at the secondary can be sensed and interpreted. For instance, the resonance frequency or the quality factor of the resonator may change depending on the effective permittivity and permeability of the secondary layer. Properties of the sample may then be determined based on the changes in the properties of the secondary layer sensed by the resonator sensor. This may enable more effective or accurate sensing by the sensor than would be possible without the secondary layer. The secondary layer may increase the surface area and adsorb more target molecules compared to a bare resonator plane or substrate, and thus may create a more discernable change in electrical properties of the secondary layer. This may allow for more accurate or higher resolution sensing.

In some embodiments, alternatively or additionally, a change in the thickness of the secondary layer can occur in response to exposure to the gas or liquid, possibly indicative of a chemical reaction. The change in thickness may cause a frequency shift or variation of quality factor at the resonator.

In some embodiments, the secondary layer may comprise a microfluidic structure, which may be used to facilitate the sensing by guiding and controlling a fluid (flowing, mixing, separating, etc. to be sensed. Microfluidic structures may be used to separate different concentrations for sensing, combine fluids, or separate the fluidics, or separate solid and liquids. Microfluidic channels may be used to mix or separate gas within a liquid or their mixture with solid particles. The integration of such a secondary layer with the resonator may be then used to monitor the behaviour of the mixture, the separation or deposition.

In addition, the secondary layer may take any solid or porous form, including but not limited to nano particle, nanotube or nano-porous forms; planar films, cubes, hemisphere particles, sets of wires, embedded microfluidic channels, micro beads, porous films, absorbent polymers, etc. In some embodiments, the secondary layer may comprise a combination of different materials, materials in different forms, or materials in different shapes.

In some embodiments, the secondary layer defining a sensing interface may be lossy. The signal loss caused by secondary layer may be compensated by the active regenerative feedback loop to enable high resolution sensing. In some embodiments, the active regenerative feedback loop may enable an increased field of view, which may in turn allow the secondary layer to be separated from the sensor with a gap.

Figure 20:
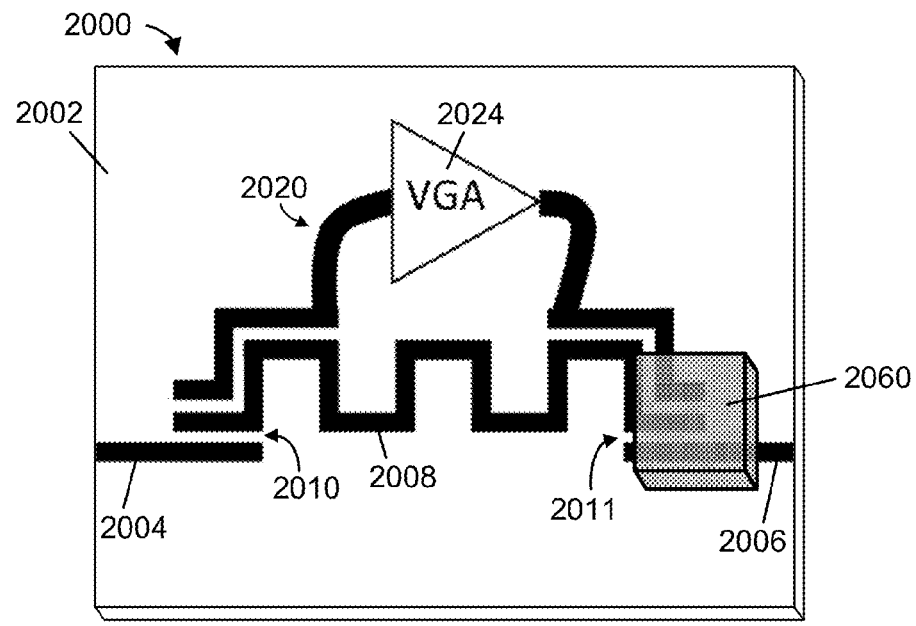
FIG. 20 is a schematic of an example planar microwave resonator comprising a secondary layer defining a sensing interface.

FIG. 20 shows an example embodiment having a planar microwave resonator 2000 comprising an active feedback loop 2020. A material 2060 is positioned in proximity to resonator 2000 to serve as a secondary layer. In this embodiment, secondary layer 2060 is shown is alignment with one of the coupling gaps of resonator 2000 (gap 2011) since this area is generally one of the most sensitive areas to variations in the ambient. Secondary layer 2060 may be positioned in contact or near contact with the surface of resonator 2000, or may be positioned at a distance from the surface of resonator 2000.

Resonator 2000 further comprises feed lines 2004 and 2006, resonator loop 2008, and may be fabricated on substrate 2002. An active device in feedback loop 2020, such as an amplifier 2024, may have one or more feed lines (not shown) for supplying electricity or controls to the amplifier. In some embodiments, resonator 2000 may be similar or identical to resonator 100 shown in FIG. 1.

It is to be appreciated that the shape, size, and composition of secondary layer 2060 and its alignment and orientation to resonator 2000 shown in FIG. 20 are provided only as an example.

A planar microwave resonator comprising of active regenerative feedback loop in combination with a secondary layer may be used in various applications. These may include but are not limited to gas emissions sensing and monitoring, including biomedical and health as lab on chip, in the oil industry, paint manufacturing, car-painting, air filter monitoring, military applications, such as gas mask filter monitoring, monitoring of adsorbents, gas trapping applications, and pollutant monitoring.

In some embodiments, the resonator may be configured for use in gas sensing applications. The permittivity of low concentrations of target gas molecules is typically not detectable by a bare microwave resonator. Therefore a separation process may be performed to enable gas sensing, in which an adsorbent (e.g. a secondary layer) is positioned at or proximate the resonator. Compounds in a gas are absorbed on the adsorbent and changes in dielectric properties of the loading adsorbent can be sensed by the resonator.

Adsorption occurs on the surface of adsorbent, therefore surface properties such as surface area and polarity play important roles in adsorption. To have a high adsorption capacity, an adsorbent typically contains a high surface area or high porosity. Depending on the size, porosity may be categorized into three groups: micropores (less than 2 nm), mesopores (between 2 and 50 nm) and macropores (larger than 50 nm). Micropores are filled at low vapor pressures through pore filling mechanism. For larger pores, such as mesopores, capillary condensation is the dominant adsorption mechanism where molecules condense on the layer of molecules previously adsorbed on the surface of the pore. Accordingly, adsorption may enhance gas sensing by accommodating a concentration of gas molecules in a small volume.

In adsorption, the target gas molecules penetrate into the pores and change the permittivity and electromagnetic conductivity of the blank adsorbent. The variation in the adsorption material may be detected by the microwave resonator as an indication of the target gas concentration. Different gas concentrations create different variations in permittivity and resistivity, which may be characterized as variations in the quality factor and resonance frequency of the resonator.

Accordingly, a planar microwave resonator according to the present disclosure may be used for high permittivity resolution, non-contact gas sensing applications. A noncontact operation of a sensor may be used for dangerous and toxic gas detection since the sensing platform does not need to be in the gas-flowing medium. Furthermore, a planar microwave resonator sensor has a small footprint and is compatible with CMOS integrated circuits, which makes it implantable in small devices and systems, for example in handheld devices, gas masks, and environmental monitoring systems, to name a few.

Experiment 4

A fourth experiment demonstrated the use of a secondary layer in combination with an active feedback loop-assisted planar microwave resonator for performing non-contact gas sensing. Various types of secondary layers may be used. Any secondary layer that can absorb organic vapours such as zeolite bead may be used. Here two different secondary layers in the form of microbeads were used separately in gas sensing to measure the concentrations of organic vapors in the gas. The active feedback loop was used to compensate the energy loss in the resonator and to create a high quality factor in the resonator.

Figure 21:
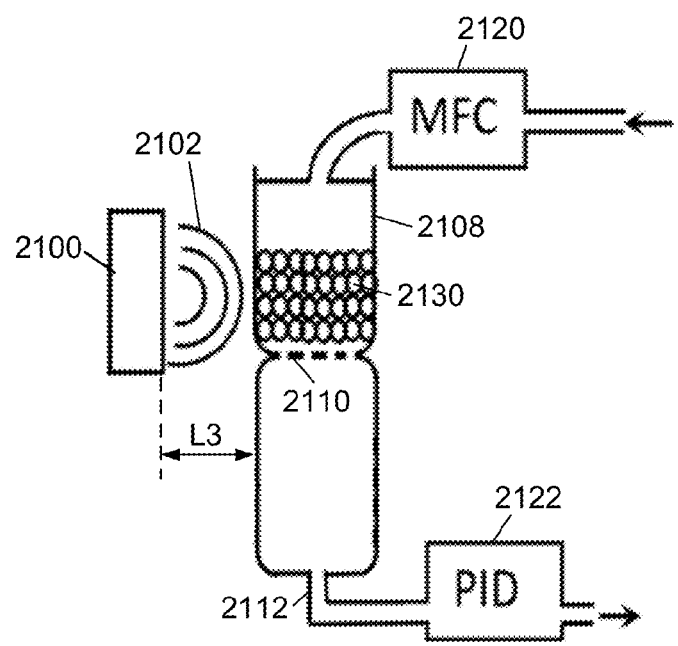
FIG. 21 is a side view of an example setup for gas sensing using a planar microwave resonator sensor.

FIG. 21 is a diagram representing the setup used in the experiment comprising a sensor 2100 having a split-ring planar microwave resonator, and a cylindrical container 2108 holding microbeads 2130 located a distance L3 from sensor 2100. In the experiment, container 2108 was positioned approximately 1 cm from sensor 2100 (e.g. L3=1 cm). Accordingly, sensor 2100 was not located in the gas-flowing medium. Lines 2102 represent an electric field generated by sensor 2100.

A flow of gas of known concentrations was induced through container 2108 in the direction of the arrows indicated in FIG. 21. As the gas passed over microbeads 2110 in container 2108, gas particles were adsorbed on the beads, which acted as an adsorbent. Changes in complex permittivity of the adsorbent were detected by the sensor and interpreted as an indication of the gas concentration. The parameters include but are not limited to resonance frequency and quality factor of the resonator. In this way, the microbeads were used as a secondary layer for performing sensing using planar resonator sensor 2100.

The experiment set-up further comprised a vapor generation system, a gas detection system, and a data acquisition and control system. These are not shown in FIG. 21 for the sake of simplicity. Container 2108 in the form of an adsorption tube was made of quartz (2.2 cm inner diameter) filled with microbeads. A fritted glass disk 2110 held the bead in place.

The vapor generation system comprised a syringe pump (KD Scientific, KDS-220) that injected liquid solvent into a dry, 20 standard liters per minute (SLPM, measured at 25° C. and 1 atm) air stream to achieve the desired inlet concentration, ranging from 35 to 695 ppm. The air flow rate was set using a mass flow controller 2120 (MFC, Alicat Scientific). The gas detection system consisted of a photoionization detector 2122 (PID, Minirae 2000, Rae Systems) that monitored volatile organic compound (VOC) concentration at outlet 2112 of adsorption tube 2108.

PID 2122 was calibrated before each test using the adsorbate stream generated with the vapor generation system. Both types beads (referred to as secondary layer bead A and secondary layer bead B), were fully loaded during all adsorption experiments, as measured by PID 2122. The data acquisition and control (DAC) system consisted of a LabVIEW program (National Instruments) and a data logger (National Instruments, Compact DAC) equipped with analog input and output modules for recording outlet VOC concentration.

Figure 22:
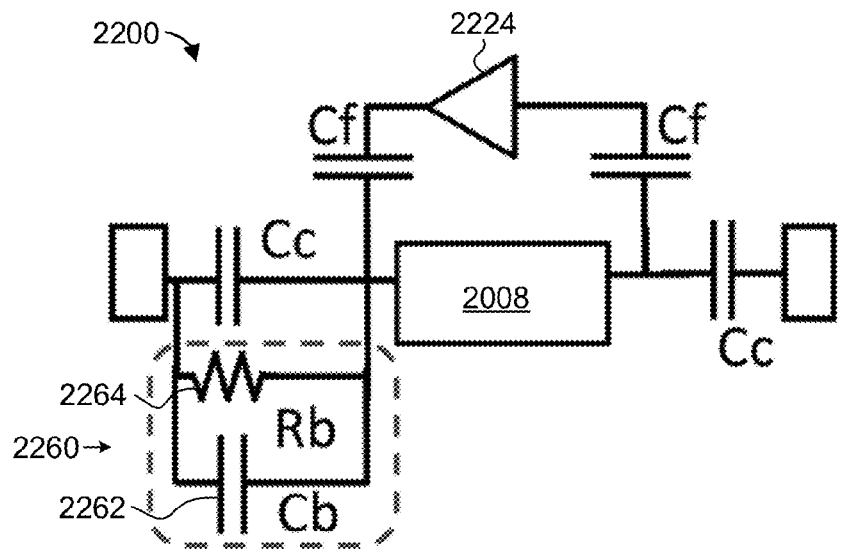
FIG. 22 is a circuit model for a resonator sensor and an absorbent material.

FIG. 22 is a circuit model for the resonator sensor 2200 and the absorbent material. Sensor comprises resonator loop 2008 and an active device 2224 in an active feedback loop. Capacitors Cc represent the coupling gap between the feed lines of the sensor and resonator loop 2008, while capacitors Cf represent the coupling gap between feedback feed lines and resonator loop 2008.

The electrical properties of the adsorbent material were modeled as a parallel RC circuit 2260 where the change in the permittivity affects the capacitor Cb 2262 and variation in the loss tangent impacts the resistor Rb 2264. The beads are a lossy material with a higher permittivity than air, therefore the equivalent permittivity in that medium can be considered as $\varepsilon=\varepsilon'-j\varepsilon''$, where $\varepsilon''$ is representative of loss in the ambient. Loss tangent is a related quantity for a lossy material which is defined as $$\tan\delta = \frac{\varepsilon''}{\varepsilon'} \tag{11}$$

According to equation (11) a relation between complex permittivity and loss tangent can be drawn $$\varepsilon=\varepsilon'(1-j\tan\delta) \tag{12}$$

Substituting equation (12) into a capacitor model, a parallel RC circuit with $Cb \propto \varepsilon'$ and $=1/C\cdot\omega\cdot\tan\delta$.

Therefore, changes in effective complex permittivity affect the resonance frequency as well as the quality factor of the sensor through variations of Cb and Rb. Sensor 2100 enables the real time monitoring of the microwave behavior of beaded adsorbents in terms of loss and permittivity as shown in FIG. 3.

During the experiments, the DC bias voltage of active device 2224, which determines the quality factor of the sensor, was kept constant at 750 mV for the measurements. The quality factor of the bare resonator, meaning without any sample material, was measured to be around 900K at the resonance frequency of 1.42 GHz. Having such a high quality factor significantly reduced the minimum detectable variations in the electrical permittivity, as shown in the following equation, and increases the resolution of the sensor.

$$|\Delta\varepsilon_{min}| = \frac{9\varepsilon\sqrt{3}}{2V_{omax}Q} \times \sqrt{4kTBR} \tag{13}$$

where $k=1.38\times10^{-23}$, T is the room temperature in Kelvin, B is the measured bandwidth, R is the resistivity of the device, s is the permittivity and $V_{omax}$ is the maximum amplitude of the resonance profile.

The scattering parameters (S21) were measured using a vector network analyzer (VNA-E8362) from Agilent. Real time measurements were performed while the gas was flowing inside adsorption tube 2108 in the vicinity of resonator 2100, and automated data acquisition was performed using Labview software. The scattering parameters were measured and recorded every one minute until beads 2130 reached their saturation point and the output gas concentration from the tube became equal to the input gas concentration. The saturation time for the beads depended on the initial concentration of the input gas and varies for different concentrations. The longest duration was measured to be 8 hours for the lowest relative pressure of 0.03.

Figure 23:
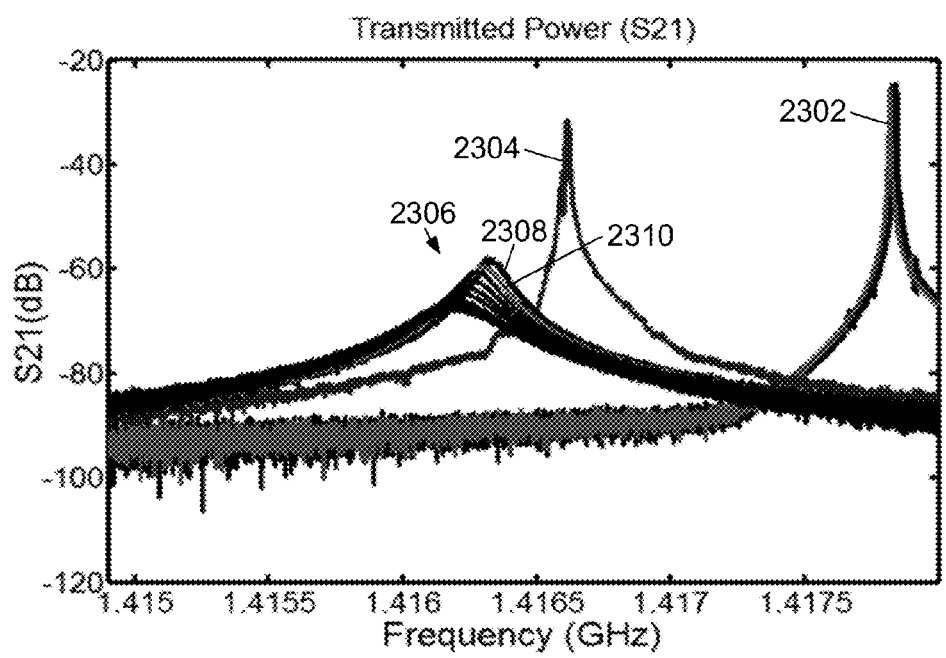
FIG. 23 is a graph of S21 scattering parameter measurements for a resonator sensor for different media in the presence of the resonator.

FIG. 23 shows S21 scattering-parameter measurements for resonator sensor 2100 for different media in the presence of the resonator. Line 2302 represents the results for air (e.g. before tube 2108 is positioned proximate resonator 2100), line 2304 represents the results when adsorption tube 2108 with bead A 2130 is positioned proximate resonator 2100 but no gas has been introduced, and lines 2306 represent a time based response of the sensor to a constant concentration of gas in the adsorption tube. For instance, line 2308 represents an S21 measurement at time t1, while line 2310 represents an S21 measurement at a later time, time t2.

Resonator sensor 2300 in air, meaning with no adsorbing material in proximity, showed a quality factor of approximately 268,000 at a resonance frequency of 1.4178 GHz. This measurement was performed several times prior to experiments and the resonance frequency and quality factor of the sensor was kept constant in all measurements. Adsorption tube 2108 (quartz crystal with activated carbon beads) was placed at a constant distance from the sensor. Since the beads are lossy, meaning they have a higher permittivity relative to air, the measured quality factor and resonance frequency drop to 110,000 and 1.4167 GHz, respectively. It was shown that introducing gas to adsorption tube 2108 affects the complex permittivity seen by the resonator, and creates a down shift in the frequency response of the sensor.

Figure 24:
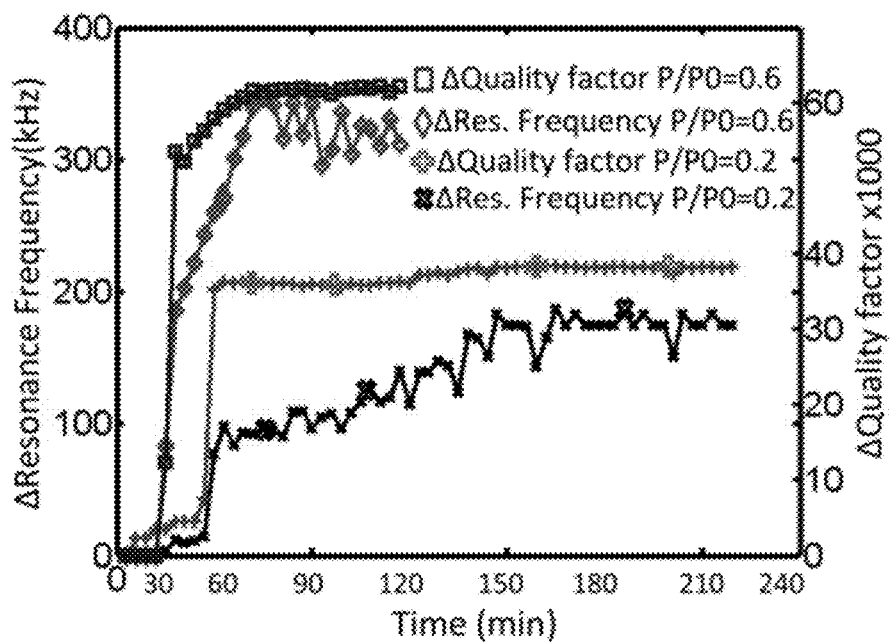
FIG. 24 is a graph of both resonance frequency and quality factor measurements plotted against time in a test in which a secondary layer was used as the adsorbent material and two different relative vapor pressures were compared.

FIG. 24 is a graph of resonance frequency and quality factor plotted against time in a test in which both beads A and B were used as the adsorbent material and two different relative vapor pressures (P/P0) of 0.2 and 0.6 were compared. More changes in frequency and quality factor were observed for higher vapor pressures, which represent the higher concentrations of gas. High concentrations of gas showed faster response times than lower concentrations, which are explained by the adsorption mechanism. During our experiments, for P/Po=0.6 to P/Po=0.2 settling times between 1 hour and 24 hours were recorded.

Figure 25:
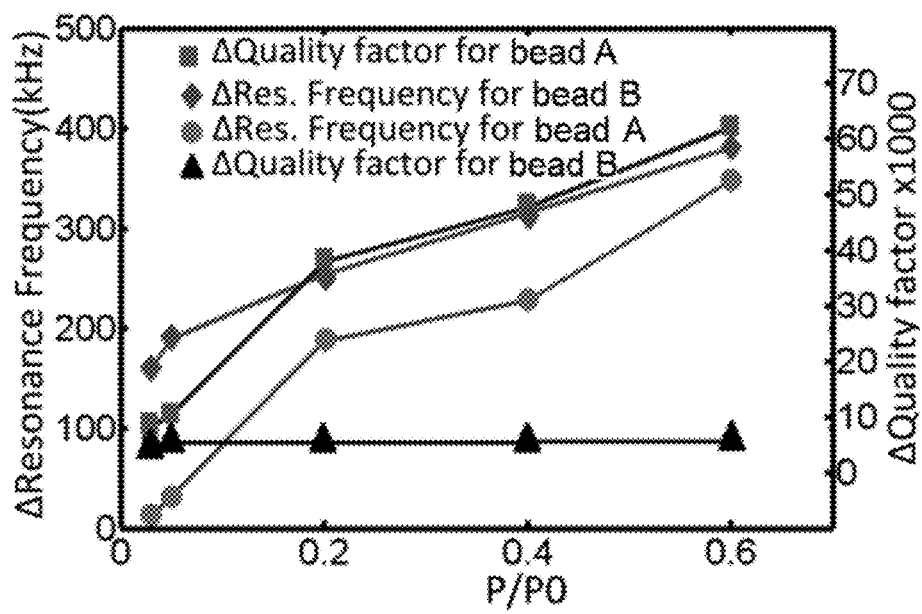
FIG. 25 is a graph of both resonance frequency and quality factor measurements for two different types of beads A (lossy) and beads B polymeric.

The same test was performed for the secondary layer bead B, which is polymeric adsorbent in various gas concentrations for the same adsorbate, and the resonance frequency shift after settling was recorded (settling time varies between 1 hour to 20 hours for P/Po=0.6 to P/Po=0.03). The results were compared with those of beads A that are lossy beads described in the previous test and are presented in FIG. 25.

According to the measurements, it was shown that beads A have higher loss compared to polymer based beads B, but polymeric beads B showed a greater shift in resonance frequency, which demonstrates the difference in their adsorption behavior. Furthermore, polymeric beads showed more swelling than carbon beads. Since the microwave sensor is a volumetric device, the higher swelling of the polymeric beads contributed to a greater shift in the resonance frequency when compared with beads A. This experiment demonstrated that a secondary layer can be used to detect different gasses and the resonator parameter can change depending on the secondary layer as facilitator and VOC gas and the sample under test.

Separate Resonator and Active Feedback Loop Components

In another aspect, the present disclosure is directed to a planar microwave resonator sensor comprising separate resonator and active feedback loop components that may be constructed on two different support structures and indirectly connected through electromagnetic, electrical or magnetic coupling.

The active component may be connected to a first coupler and the passive resonator component may be connected to a second coupler. This may be contrasted with some previously described embodiments where feedback lines of a feedback loop are located in close proximity to and on the same substrate as the passive resonator loop.

In some embodiments, each of the passive resonator and the active feedback loop may be positioned on separate substrates or other support structures, which allows the resonator to be positioned in a spaced apart relationship from the active feedback loop. This may be used in applications where there is a need or benefit to separate the resonator from the active feedback loop. For instance, a passive resonator may be installed directly in a dangerous or harsh environment while the active feedback loop and possibly other components are installed in a safer location. For example, a passive resonator component may be installed on the interior of a pipe or container while the active feedback loop is installed on the exterior and therefore is not exposed to the contents of the pipe or container. As another example, the passive resonator may be an implantable sensor for real time monitoring of biological or physiological parameters of a live animal or human where the active part is used outside of the body where it is easier to access.

Figure 26:
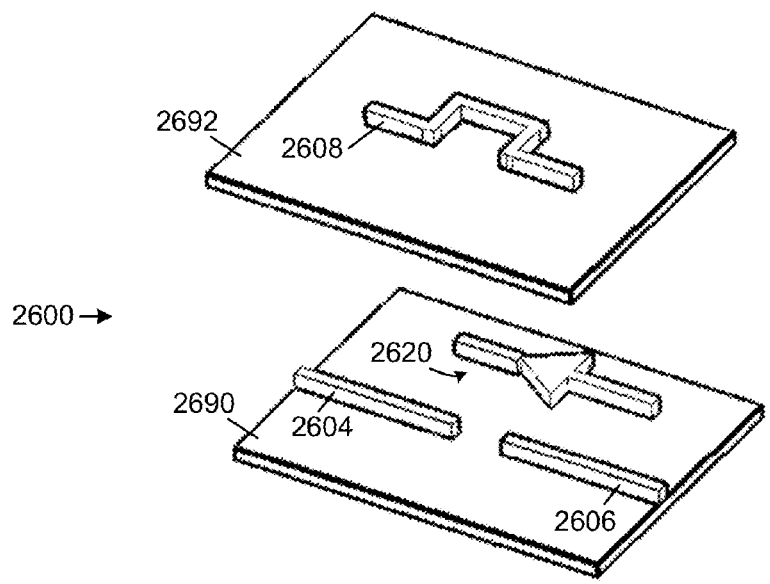
FIG. 26 is a diagram of an example planar microwave resonator sensor comprising an active feedback loop and a resonator in different physical layers.

FIG. 26 is a block diagram representing an example planar microwave resonator sensor 2600 comprising an active feedback loop 2620 in a first layer 2690 (or plane), and a resonator 2608 in a second layer 2692 (or plane) that is physically spaced apart from first layer 2690. In this embodiment, passive resonator 2608 is capacitively coupled to active feedback loop 2620 and one or more feed lines 2604 and 2606 by virtue of layers 3092 and 3090 being physically separated. Second layer 2692 may include other components, such as feed lines 2604 and 2606. Layers or planes 2690 and 2692 represent planes or layers in space, and not necessarily any physical structure. However, in some embodiments, a layer may be in the form of a substrate or other support structure for supporting various circuit components.

Figure 27:
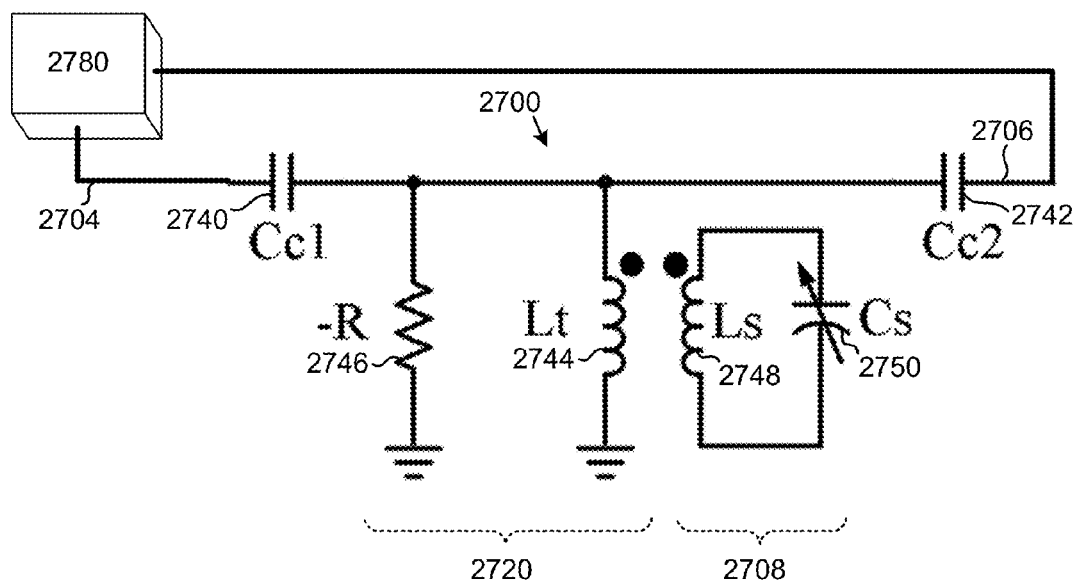
FIG. 27 is a circuit diagram of an example planar microwave resonator sensor where separate active feedback and passive resonator components are electromagnetically coupled using additional coupling elements.

FIG. 27 is a circuit diagram of an example planar microwave resonator sensor 2700 having a passive resonator component 2708 and an active feedback loop component 2720 that may be electromagnetically coupled using additional coupling elements 2748 and 2744.

Active feedback loop component (e.g. regeneration circuit) 2720 may be physically separated from sensor resonator component 2708. To establish a magnetic or electric or electromagnetic coupling between the separated components, an inductive or capacitive or resonance inductive coupling may be used. System coupling capacitors Cc1 2740 and Cc2 2742 represent capacitive couplings (e.g. coupling gaps) between feed lines of sensor 2704 and 2706, and feedback loop 2720 and resonator 2708, which establish an AC signal coupling to the sensor device. Inductor Lt 2744 may be used as a transmitter coil. The negative resistance provided by active feedback loop 2720 is modeled here by (−R) 2746 and may be connected to a DC supply voltage for operation. The regenerative active device (e.g. amplifier) may consume high power and create heat, which is undesired for some applications, such as certain biomedical and hazardous applications. Accordingly, passive sensing resonator 2708 may be physically separated from the active feedback loop components.

Sensing resonator 2708 comprises inductor Ls 2748, and capacitor Cs 2750 which may serve as the sensing device. In addition to serving as a resonant component, Ls 2748 may also be used as a receiver coil to establish the electromagnetic coupling between resonator 2708 and active feedback loop 2720.

In some embodiments, the roles of inductor Ls 2748 and capacitor Cs 2750 may be reversed. For instance, a capacitive coupling may be established between resonator 2708 and active feedback loop 2720 rather than an inductive coupling. In such an embodiment, capacitor Cs 2750 may be used as a coupling device and inductor Ls 2748 may be used as a sensing device.

Furthermore, resonator 2700 may be used in combination with other equipment or components 2780, which may be connected to one or more feed lines 2704 and 2706 of resonator sensor 2700. Other equipment 2780 may comprise one or more of a processor, a microcontroller, a volatile memory, a non-volatile memory, a network analyzer, a communications system, a microwave oscillator, a signal processing system, a data storage system, a computing device, analog circuitry, etc. However, this other equipment and other component(s) 2780 are not shown in any detail for the sake of simplicity.

Figure 28:
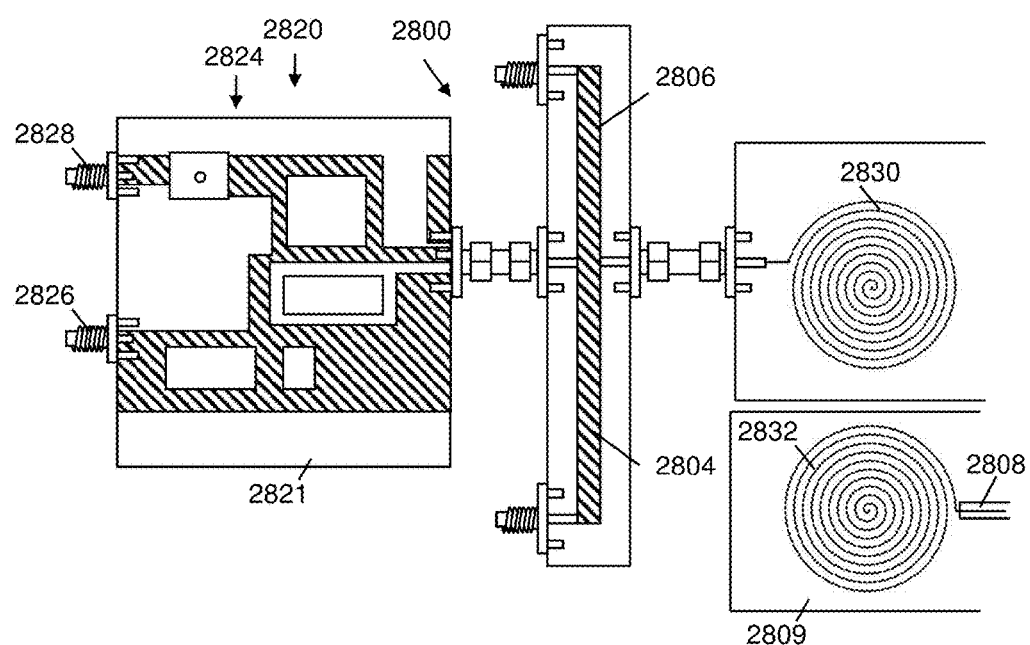
FIG. 28 is an example embodiment of a planar microwave resonator sensor similar to the diagram of FIG. 27.

FIG. 28 is an example embodiment of a resonator sensor 2800 according to the present disclosure. Resonator sensor 2800 comprises feed lines 2804 and 2806 (or "ports"), active feedback loop 2820, direct current (DC) feeds 2826 and 2828 to active device 2824, such as an amplifier, and a separate resonator 2808. Resonator 2808 may be located or formed on a first substrate or support structure 2809, while active feedback loop 2820 may be located or formed on a second substrate or support structure 2821. separate from first substrate 2809. Active feedback loop 2820 and feed lines 2826 and 2828 are electrically coupled to first electromagnetic coupling element 2830, and resonator 2808 is electrically coupled to second electromagnetic coupling element 2832.

Active feedback loop 2820 may be electromagnetically coupled to resonator 2808 through first and second coupling elements 2830 and 2832 when coupling elements 2830 and 2832 are positioned in proximity to one another (not shown). For example, coupling elements 2830 and 2832 may be positioned in at least a partly overlapping relationship (not shown).

A microwave signal may be applied to feed line 2826 or 2828 to excite planar microwave resonator 2808 through an electromagnetic coupling between first and second coupling elements 2830 and 2832. In response to the excitation of resonator 2808 in proximity to the sample, one or more of resonance frequency, quality factor, and amplitude of a signal of resonator 2808 may be measured at first or second feed line 2826 or 2828.

Coupling elements 2830 and 2832 are shown in the form of inductive coils, but any other suitable type of electromagnetic coupling element may be used.

In some embodiments, both substrate or support structure 2809 and resonator 2808 may be sensitive to the sample under investigation (e.g. gas, liquid, solid, etc.). For example, layer 2692 (or layer 2690) may also be sensitive to the parameters that are to be sensed. In such a situation, the layer may play a role similar to a secondary layer described above, which may be used to facilitate sensing. A layer or substrate may be made from one or more various materials, such as solid substrates, swelling polymers, porous films or tubes, microfluidic chip, etc.

In some embodiments, a resonator sensor comprising separate resonator and active feedback loop components that may be electromagnetically coupled may also be operated to compensate for the loss of the sample or the environment as described above in relation to other embodiments.

Furthermore, in some embodiments, a resonator sensor comprising electromagnetically coupled resonator and active feedback loop components may be used in combination with a second layer acting as a sensing interface, as previously described in relation to other embodiments.

Experiment 5

A fifth experiment demonstrated the use and operation of a resonator sensor comprising separate and electromagnetically coupled resonator and active feedback loop components. Here, a separate resonator was magnetically coupled to the active feedback loop. The setup used this experiment is the one shown in FIG. 28.

Figure 29A:
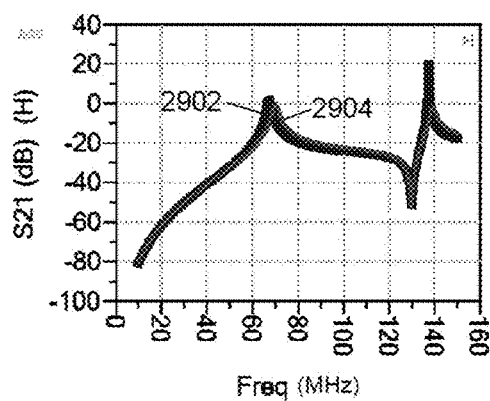
FIG. 29A is a graph showing S21 scattering parameter measurements of a resonator sensor with its active feedback loop turned off both with and without a test sample.

FIG. 29A is a graph showing S21 scattering parameter measurements of resonator sensor 2800 with active feedback loop 2820 turned off both without and with a test sample of carbon beads positioned in proximity to resonator 2808. Line 2902 represents the results without the sample present, while line 2904 represents the results with the sample present. The quality factor of the resonator was approximately 90 in passive mode.

Figure 29B:
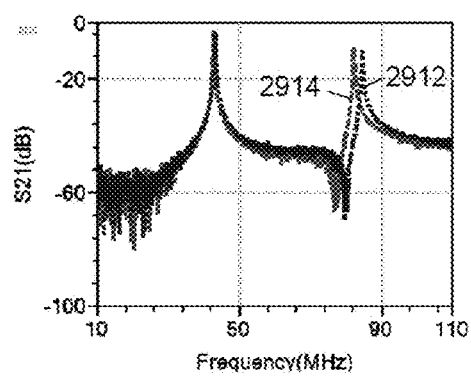
FIG. 29B is a graph showing S21 scattering parameter measurements of the resonator sensor with its active feedback loop turned on both with and without a test sample.

FIG. 29B is a graph showing S21 scattering parameter measurements of resonator sensor 2800 with active feedback loop 2820 turned on both without and with the test sample positioned in proximity to resonator 2808. In this figure, line 2912 represents the results without the sample present, while line 2914 represents the results with the sample present. The quality factor of the resonator was measured to be approximately 2700. In contrast, the quality factor was only 90 with the active feedback loop turned off. Again, the active feedback loop increased the quality factor of the resonator sensor, which generally allows for more accurate and higher resolution permittivity sensing.

The apparatuses, devices and methods according to the present disclosure may be used as part of or in conjunction with a larger sensor or sensing system. In addition, a sensor may comprise two or more resonators, where at least some of the resonators have different resonant frequencies.

Furthermore, the apparatuses, devices and methods according to the present disclosure may be used in various applications, including but not limited to applications relating to material identification, measuring or monitoring precipitation in a liquid, measuring or detecting chemical fouling, counting biological cells, distinguishing between cells, detecting nano particles, measuring or sensing the size of nano particles, measuring liquid concentrations, measuring a chemical concentration in a water based solution, monitoring the variation of lossy or non-lossy chemical behavior over time, biomedical diagnostics, pH or pOH sensing, microfluidics, real-time monitoring of adsorbents performance in gas trapping, pollutant monitoring, sensing or monitoring in harsh or unreachable environments, down the hole chemical or environmental monitoring for oil or gas applications, and implantable bio sensors for physiological or biological monitoring and sensing in real time.

The term "proximity" as used herein to refer to a distance between a resonator and a sample or other medium is not intended to be limited to any specific minimum or maximum distance or distances, unless specifically indicated. Furthermore, although the term is generally used to refer to a non-zero distance, meaning a non-contact sensing setup, it may sometimes include a distance of zero where the sample or medium is in contact with the resonator.

Although the methods and processes described and illustrated in the present disclosure each show a particular number and order of operations in their respective processes, this is not meant to be limiting. One or more of the order of the operations, the number of operations, and the operations themselves may be different in other embodiments. Thus the present embodiments are only examples and are not meant to be limiting.

Furthermore, the particular experiments, resonators, samples and their parameters and other values described in the present disclosure are meant as examples only and are thus not intended to be limiting.

Through the descriptions of the preceding embodiments, the teachings of the present disclosure may be implemented by using hardware only or by using a combination of software and hardware. Software or other computer executable instructions for implementing one or more embodiments, or one or more portions thereof, may be stored on any suitable computer readable storage medium. The computer readable storage medium may be a tangible or in transitory/non-transitory medium such as optical (e.g., CD, DVD, Blu-Ray, etc.), magnetic, hard disk, volatile or non-volatile, solid state, or any other type of storage medium known in the art.

One or more of the structure, features, accessories, alternatives, and applications of general or specific embodiments described herein and or shown in the Figures are intended to apply generally to all of the teachings of the present disclosure, including to all of the embodiments described and illustrated herein, insofar as they are compatible. In other words, the structure, features, accessories, alternatives, and applications of a specific embodiment are not intended to be limited to only that specific embodiment unless so indicated.

Reference(s) to an element in the singular, such as by use of the article "a" or "an" is not intended to mean "one and only one" unless specifically so stated, but rather "one or more".

The present disclosure is provided to enable any person skilled in the art to make or use the present teachings. Various modifications to embodiments described herein will be readily apparent to those skilled in the art, and the generic principles defined herein may be applied to other embodiments. The present disclosure is not intended to be limited to the embodiments shown herein, but is to be accorded the full scope consistent with the claims. All structural and functional equivalents to the elements of the various embodiments described throughout the disclosure that are known or later come to be known to those of ordinary skill in the art are intended to be encompassed by the elements of the claims.

Nothing disclosed herein is intended to be dedicated to the public regardless of whether such disclosure is explicitly recited in the claims. Furthermore, nothing herein is intended as an admission of prior art or of common general knowledge. In addition, citation or identification of any document in this application is not an admission that such document is available as prior art, or that any reference forms a part of the common general knowledge in the art.

The following clause(s) describe further aspects of the present disclosure:

C1. A method for microwave sensing of a sample, the method comprising:
  positioning a passive planar microwave resonator in proximity to the sample, the planar microwave resonator disposed at a first support structure and electrically connected to a first electromagnetic coupling element;
  positioning a second electromagnetic coupling element in proximity to the first electromagnetic coupling element, the second electromagnetic coupling element electrically connected to first and second feed lines, and to an active feedback loop, the active feedback loop disposed at a second support structure separate from the first support structure;
  applying a microwave signal at the first or second feed line to excite the planar microwave resonator through an electromagnetic coupling between the first and second electromagnetic coupling elements, where a quality factor of the resonator is increased by the active feedback loop; and
  measuring at least one of resonance frequency, quality factor, and amplitude of a signal of the planar microwave resonator at the first or second feed line in response to the excitation of the resonator in proximity to the sample.

What is claimed:

1. A method for high resolution microwave sensing of a sample in the presence of a lossy medium, the method comprising:
  increasing the quality factor of a passive planar microwave resonator to a first value with an active regenerative feedback loop;
  positioning the lossy medium and the planar microwave resonator in proximity to one another, thereby decreasing the quality factor of the planar microwave resonator to a second value;
  adjusting the active feedback loop to compensate for signal energy loss of the planar microwave resonator due to the lossy medium, where the adjusting raises the quality factor to a third value that is higher than the second value;
  positioning the sample and the planar microwave resonator in proximity to one another such that the resonator signal passes through the lossy medium to sense the sample variation; and
  measuring at least one of resonance frequency, quality factor, and amplitude of a signal of the planar microwave resonator in response to the excitation of the resonator in proximity to the sample.

2. The method of claim 1, wherein the adjusting the active feedback loop involves adjusting a direct current bias voltage of an amplifier of the active feedback loop.

3. The method of claim 1, further comprising measuring a variation in at least one of resonance frequency, quality factor, or amplitude of a signal of the planar microwave resonator.

4. The method of claim 1, wherein the lossy medium has a higher permittivity compared to a vacuum.

5. The method of claim 1, wherein the lossy medium comprises a liquid.

6. The method of claim 1, wherein the planar microwave resonator is a meandered split ring resonator.

7. A method for microwave sensing of a sample, the method comprising:
  positioning a passive planar microwave resonator in proximity to the sample, the planar microwave resonator disposed at a first support structure, wherein the planar microwave resonator is electromagnetically, electrically or magnetically coupled to a second resonator to form an additional resonant frequency, the second resonator having its own resonance and being disposed at a second support structure separate from the first support structure and having at least one feed line and an active feedback loop;
  applying a microwave signal at the feed line to excite the planar microwave resonator through the coupling between the passive planar microwave resonator and the second resonator, where a quality factor of the additional resonant frequency is increased by the active feedback loop on the second support structure; and measuring at least one of resonance frequency, quality factor, and amplitude of the additional resonant frequency at the feed line in response to the excitation of the second resonator.

8. The method of claim 7, wherein the first and second support structures are positioned in different spatial planes.

9. The method of claim 7, wherein the first support structure comprising the planar microwave resonator is positioned on a first side of a structure, and the second support structure comprising the second resonator and the active feedback loop and the feed line is positioned in proximity on a second opposing side of the structure.

10. The method of claim 9, wherein the first support structure comprising the planar microwave resonator is positioned within an enclosing structure, and wherein the second support structure comprising the second resonator and the active feedback loop and the feed line is positioned on the exterior of the enclosing structure.

11. The method of claim 7, further comprising adjusting the active feedback loop for increasing the quality factor of the resonator.

12. The method of claim 11, wherein the adjusting comprises adjusting the active feedback loop to compensate for signal energy loss of the planar microwave resonator due to the lossy nature of at least one of the sample and an environment in which the sample is located.

13. The method of claim 7, further comprising:
positioning a secondary layer proximate to a planar microwave resonator;
exposing the secondary layer to the sample or physical stimulation; and
measuring, after the exposing, at least one of resonance frequency, quality factor, and amplitude of a signal of the planar microwave resonator in response to the exposure of the secondary layer to the sample and excitation of the resonator in proximity to the secondary layer.

14. The method of claim 7, further comprising calculating a permittivity related parameter of the sample based on the measured at least one of resonance frequency, quality factor, and amplitude of the resonator.

* * * * *